(12) United States Patent
Ramamoorthy

(10) Patent No.: US 7,129,237 B2
(45) Date of Patent: Oct. 31, 2006

(54) [1,4]DIAZEPINO[6,7,1-IJ]QUINOLINE DERIVATIVES AS ANTIPSYCHOTIC AND ANTIOBESITY AGENTS

(75) Inventor: P. Sivaramakrishnan Ramamoorthy, Plainsboro, NJ (US)

(73) Assignee: Wyeth, Madison, NJ (US)

( * ) Notice: Subject to any disclaimer, the term of this patent is extended or adjusted under 35 U.S.C. 154(b) by 185 days.

(21) Appl. No.: 10/422,524

(22) Filed: Apr. 24, 2003

(65) Prior Publication Data

US 2004/0009970 A1    Jan. 15, 2004

Related U.S. Application Data

(60) Provisional application No. 60/375,592, filed on Apr. 25, 2002.

(51) Int. Cl.
A61P 25/18   (2006.01)
C07D 487/22  (2006.01)
A61K 31/55   (2006.01)

(52) U.S. Cl. ............................ 514/219; 540/555
(58) Field of Classification Search ............... 514/219; 540/555
See application file for complete search history.

(56) References Cited

U.S. PATENT DOCUMENTS

| | | | |
|---|---|---|---|
| 3,158,619 A | 11/1964 | Wagner | 260/310 |
| 3,235,564 A | 2/1966 | Wagner | 260/327 |
| 3,296,252 A | 1/1967 | Frey et al. | 260/239.3 |
| 3,329,676 A | 7/1967 | Bell et al. | 260/239.3 |
| 3,335,134 A | 8/1967 | Frey et al. | 260/239.3 |
| 3,417,101 A | 12/1968 | Bell et al. | 260/328 |
| 3,466,274 A | 9/1969 | De Ridder | 260/239 |
| 3,714,149 A | 1/1973 | Hester, Jr. | 260/239.3 T |
| 3,914,250 A | 10/1975 | Kim | 260/315 |
| 4,880,814 A | 11/1989 | Chu et al. | 546/123 |
| 4,997,831 A | 3/1991 | Bays et al. | 514/211 |
| 5,045,545 A | 9/1991 | Bays et al. | 514/284 |
| 5,834,454 A | 11/1998 | Kitano et al. | 514/183 |
| 6,414,144 B1 | 7/2002 | Welmaker et al. | 540/555 |
| 6,503,900 B1 | 1/2003 | Sabb et al. | 514/219 |
| 2002/0055504 A1 | 5/2002 | Chan | 514/219 |
| 2002/0058689 A1 | 5/2002 | Welmaker et al. | 514/411 |
| 2002/0062022 A1 | 5/2002 | Sabb et al. | 540/556 |
| 2002/0107242 A1 | 8/2002 | Sabb et al. | 514/219 |
| 2002/0119966 A1 | 8/2002 | Sabb et al. | 514/219 |
| 2002/0128261 A1 | 9/2002 | Sabb et al. | 514/219 |
| 2002/0173503 A1 | 11/2002 | Robichaud et al. | 514/211.1 |
| 2003/0050300 A1 | 3/2003 | McWhorter, Jr. | 514/211.1 |
| 2004/0019040 A1 | 1/2004 | Ramamoorthy et al. | 514/220 |
| 2004/0034005 A1 | 2/2004 | Gao et al. | 514/183 |

FOREIGN PATENT DOCUMENTS

| | | |
|---|---|---|
| EP | 0 344 015 A2 | 11/1989 |
| EP | 0 357 417 A1 | 3/1990 |
| JP | 02-040379 | 2/1990 |
| JP | 10-237073 | 9/1998 |
| JP | 2001-89461 | 4/2004 |
| SU | 930902 | 11/1982 |
| WO | WO 90/15058 A1 | 12/1990 |
| WO | WO 96/29316 | 9/1996 |
| WO | WO 97/30999 A1 | 8/1997 |
| WO | WO 97/31000 A1 | 8/1997 |
| WO | WO 99/66934 A1 | 12/1999 |
| WO | WO 99/67219 A1 | 12/1999 |
| WO | WO 00/35922 | 6/2000 |
| WO | WO 00/40226 A2 | 7/2000 |
| WO | WO 00/64899 A1 | 11/2000 |
| WO | WO 00/77002 A1 | 12/2000 |
| WO | WO 01/12602 A1 | 2/2001 |
| WO | WO 01/12603 A1 | 2/2001 |
| WO | WO 01/64246 A2 | 9/2001 |
| WO | WO 02/08186 | 1/2002 |
| WO | WO 02/36596 A2 | 5/2002 |
| WO | WO 02/42304 A2 | 5/2002 |
| WO | WO 02/059124 A2 | 8/2002 |
| WO | WO 02/059129 A1 | 8/2002 |

OTHER PUBLICATIONS

Gregory E. Martin et al., J. Med. Chem., 32, 1052-1056 (1989).
J.L. Browning et al., Society for Neuroscience Abstracts, 25(2), 2075, Abstract 830.12, (1999).
Jackson B. Hester et al., J. Med. Chem., 13, 827-835 (1970).
Dong H. Kim, J. Heterocycl. Chem., 13(6), 1187-1192 (1976).

(Continued)

Primary Examiner—Brenda Coleman
(74) Attorney, Agent, or Firm—Kimberly R. Hild

(57) ABSTRACT

Compounds of Formula I or a pharmaceutically acceptable salt thereof are provided:

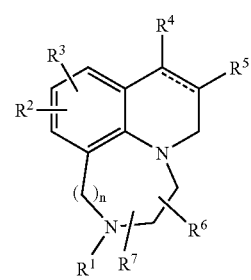

where $R^1$ through $R^7$ are defined herein. The compounds of Formula I are 5HT2c agonists or partial agonists, and are useful for treating a variety of disorders.

52 Claims, No Drawings

OTHER PUBLICATIONS

H.P. Haerter et al., Chimia, 30, 50-52 (1976).
Oliver H. Lowry et al., J. Biol. Chem., 193, 265-275 (1951).
Samuel H. Wilen, et al., Tetrahedron, 33, 2725-2736 (1977).
Shunji Naruto et al., Tetrahedron Letters, 39, 3399-3402 (1975).
Giuseppe Digiovanni et al., Synapse, 35, 53-61 (2000).
Vincenzo Dimatteo et al., Neuropharmacology, 37, 265-272 (1998).
Vincenzo Dimatteo, et al., Neuropharmacology, 38, 1195-1205 (1999).
M.J. Millan et al., Neuropharmacology, 37, 953-955 (1998).
Prakash S. Masand, Exp. Opin. Pharmacother, 1(3), 377-389 (2000).
David B. Allison et al., Am. J. Psychiatry, 156(11), 1686-1696 (1999).
P.J. Cowan et al., Human Psychopharmacology, 10, 385-391 (1995).
A. Schotte et al., Psychopharmacology, 124m 57-73 (1996).
Susan H. Fox et al., Experimental Neurology, 151, 35-49 (1998).
R. Whitaker, Spectrum, 2, 1-12 (2000).
A.N. Grinev et al., Chem. Heterocycl. Compd., 19(9), 959-961 (1983).
A.N. Grinev et al., Chem. Heterocycl. Compd., 19(12), 1312-1315 (1983).
E.V. Lamanova et al., Pharm. Chem., J., 23(2), 113-115 (1989).
D.H. Kim et al., Journal of Medicinal Chemistry, 20(2), 209-212 (1977).
L. Toscano et al., J. Heterocyclic Chem., 13, 475-480 (1976).
A. Katritzky et al., Synthesis, 10, 1487-1490 (1998).
F. Gatta et al., Edizione Scientifica, 30(8), 631-641 (1975).
W. Lopes et al., Journal of Brazilian Chemical Society, 4(1), 34-39 (1993).
S. Rosenzweig-Lipson et al., The FASEB Journal, 14, A1321 (2000).

[1,4]DIAZEPINO[6,7,1-IJ]QUINOLINE DERIVATIVES AS ANTIPSYCHOTIC AND ANTIOBESITY AGENTS

CROSS REFERENCE TO RELATED APPLICATIONS

This application claims the benefit under 35 U.S.C. §119 (e) to U.S. provisional application Ser. No. 60/375,592 filed Apr. 25, 2002, which is hereby incorporated by reference in its entirety.

BACKGROUND OF THE INVENTION

Schizophrenia affects approximately 5 million people. At present, the most widespread treatments for schizophrenia are the 'atypical' antipsychotics, which combine dopamine ($D_2$) receptor antagonism with serotonin (5-$HT_{2A}$) receptor antagonism. Despite the reported advances in efficacy and side-effect liability of atypical antipsychotics over typical antipsychotics, these compounds do not adequately treat all of the symptoms of schizophrenia and are accompanied by problematic side effects including weight gain (Allison, D. B., et. al., Am. J. Psychiatry, 156: 1686–1696, 1999; Masand, P. S., Exp. Opin. Pharmacother. I: 377–389, 2000; Whitaker, R., Spectrum Life Sciences. Decision Resources. 2:1–9, 2000). Novel antipsychotics which are effective in treating the mood disorders or the cognitive impairments in schizophrenia without producing weight gain would represent a significant advance in the treatment of schizophrenia.

5-$HT_{2C}$ agonists and partial agonists represent a novel therapeutic approach toward the treatment of schizophrenia. Several lines of evidence support a role for 5-$HT_{2C}$ receptor agonism as a treatment for schizophrenia. Studies with 5-$HT_{2C}$ antagonists suggest that these compounds increase synaptic levels of dopamine and may be effective in animal models of Parkinson's disease (Di Matteo, V., et. al., Neuropharmacology 37: 265–272, 1998; Fox, S. H., et. al., Experimental Neurology 151: 35–49, 1998). Since the positive symptoms of schizophrenia are associated with increased levels of dopamine, compounds with actions opposite those of 5-$HT_{2C}$ antagonists such as 5-$HT_{2C}$ agonists and partial agonists should reduce levels of synaptic dopamine. Recent studies have demonstrated that 5-$HT_{2C}$ agonists decrease levels of dopamine in the prefrontal cortex and nucleus accumbens (Millan, M. J., et. al., Neuropharmacology 37: 953–955, 1998; Di Matteo, V., et. al., Neuropharmacology 38: 1195–1205, 1999; Di Giovanni, G., et. al., Synapse 35: 53–61, 2000), brain regions that are thought to mediate critical antipsychotic effects of drugs like clozapine. In contrast, 5-$HT_{2C}$ agonists do not decrease dopamine levels in the striatum, the brain region most closely associated with extrapyramidal side effects. In addition, a recent study demonstrates that 5-$HT_{2C}$ agonists decrease firing in the ventral tegmental area (VTA), but not in substantia nigra. The differential effects of 5-$HT_{2C}$ agonists in the mesolimbic pathway relative to the nigrostriatal pathway suggests that 5-$HT_{2C}$ agonists will have limbic selectivity and will be less likely to produce extrapyramidal side effects associated with typical antipsychotics.

Atypical antipsychotics bind with high affinity to 5-$HT_{2C}$ receptors and function as 5-$HT_{2C}$ receptor antagonists or inverse agonists. Weight gain is a problematic side effect associated with atypical antipsychotics such as clozapine and olanzapine and it has been suggested that 5-$HT_{2C}$ antagonism is responsible for the increased weight gain. Conversely, stimulation of the 5-$HT_{2C}$ receptor is known to result in decreased food intake and body weight (Walsh et. al., Psychopharmacology 124: 57–73, 1996; Cowen, P. J., et. al., Human Psychopharmacology 10: 385–391, 1995; Rosenzweig-Lipson, S., et. al., ASPET abstract, 2000). As a result, 5-$HT_{2C}$ agonists and partial agonists will be less likely to produce the body weight increases associated with current atypical antipsychotics. Indeed, 5-$HT_{2C}$ agonists and partial agonists are of great interest for the treatment of obesity, a medical disorder characterized by an excess of body fat or adipose tissue and associated with such comorbidities as Type II diabetes, cardiovascular disease, hypertension, hyperlipidemia, stroke, osteoarthritis, sleep apnea, gall bladder disease, gout, some cancers, some infertility, and early mortality.

SUMMARY OF THE INVENTION

In one embodiment, the present invention provides compounds of Formula I or a pharmaceutically acceptable salt thereof:

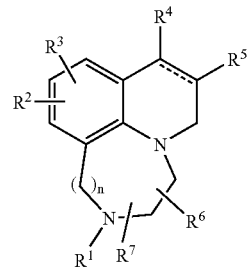

where $R^1$ is hydrogen, alkyl of 1 to 6 carbon atoms, alkanoyl of 2 to 6 carbon atoms, or carboarylalkoxy of 7 to 11 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are, independently, hydrogen or alkyl of 1 to 6 carbon atoms, or $R^4$ and $R^5$, taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms; n is 1 or 2; and a dotted line represents an optional double bond.

In another embodiment of the present invention, a method of treating a mammal suffering from a condition selected from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, intellectual deficit associated with Alzheimer's disease, bipolar disorders, depressive disorders, mood episodes, anxiety disorders, adjustment disorders, eating disorders, epilepsy, sleep disorders, migraines, sexual dysfunction, gastrointestinal disorders, obesity, or a central nervous system deficiency associated with trauma, stroke, or spinal cord injury is provided that includes administering to the mammal at least one compound of Formula I or a pharmaceutically acceptable salt thereof. In this embodiment, preferably $R^1$ of Formula I is hydrogen or alkyl of 1 to 6 carbon atoms and more preferably hydrogen.

In yet another embodiment of the present invention, a pharmaceutical composition is provided that contains at least one compound of Formula I and at least one pharmaceutically acceptable carrier or excipient, where preferably, $R^1$ of Formula I is hydrogen or alkyl of 1 to 6 carbon atoms and more preferably hydrogen.

DETAILED DESCRIPTION OF INVENTION

This invention provides compounds of Formula I or a pharmaceutically acceptable salt thereof:

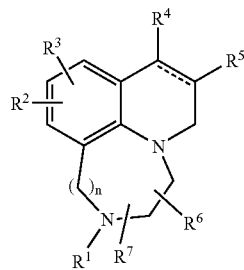

I where $R^1$ is hydrogen, alkyl of 1 to 6 carbon atoms, alkanoyl of 2 to 6 carbon atoms, or carboarylalkoxy of 7 to 11 carbon atoms, and preferably hydrogen or alkyl of 1 to 6 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are, independently, hydrogen or alkyl of 1 to 6 carbon atoms, or $R^4$ and $R^5$, taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms;

n is 1 or 2; and a dotted line represents an optional double bond.

In some preferred embodiments of the invention $R^2$ is hydrogen, halogen, cyano, perfluoroalkyl of 1 to 3 carbon atoms, alkyl of 1 to 6 carbon atoms, alkoxy of 1 to 6 carbon atoms, alkanoyl of 2 to 6 carbon atoms, alkanesulfonyl of 1 to 6 carbon atoms, or aryl of 5 to 7 carbon atoms. More preferably, $R^2$ is hydrogen, halogen, cyano, alkoxy of 1 to 3 carbon atoms, phenyl or trifluoromethyl.

In other preferred embodiments of the invention $R^3$ is hydrogen, halogen, cyano, perfluoroalkyl of 1 to 3 carbon atoms, alkyl of 1 to 6 carbon atoms, alkoxy of 1 to 6 carbon atoms, alkanoyl of 2 to 6 carbon atoms, alkanesulfonyl of 1 to 6 carbon atoms, or aryl of 5 to 7 carbon atoms. More preferably, $R^3$ is hydrogen, halogen, cyano, alkoxy of 1 to 3 carbon atoms, phenyl or trifluoromethyl.

$R^4$ and $R^5$ are preferably taken together, along with the carbon atoms to which they are attached, to form a cycloalkane or cycloalkene moiety of 5 to 8 carbon atoms, where one or more of the carbon atoms are optionally substituted by alkyl of 1 to 4 carbon atoms, and more preferably a cycloalkane moiety of 5 to 7 carbon atoms.

$R^1$, $R^6$ and $R^7$ are preferably hydrogen.

n is preferably 1.

In still other preferred embodiments of the invention, $R^2$ and $R^3$ are independently selected from hydrogen, halo, trifluoromethyl, phenyl or alkoxy of 1 to 3 carbon atoms, $R^1$, $R^6$ and $R^7$ are each hydrogen, n is 1, and $R^4$ and $R^5$, taken together with the carbon atoms to which they are attached, form cyclopentane, cyclohexane or cycloheptane.

The compounds of this invention contain asymmetric carbon atoms and thus give rise to optical isomers and diastereoisomers. While shown without respect to stereochemistry in Formula I, the present invention includes such optical isomers and diastereoisomers; as well as the racemic and resolved, enantiomerically pure R and S stereoisomers; as well as other mixtures of the R and S stereoisomers and pharmaceutically acceptable salts thereof.

Where an enantiomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. "Substantially free," as used herein, means that the compound is made up of a significantly greater proportion of one enantiomer. In preferred embodiments the compound is made up of at least about 90% by weight of a preferred enantiomer. In other embodiments of the invention, the compound is made up of at least about 99% by weight of a preferred enantiomer. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl, as used herein, refers to an aliphatic hydrocarbon chain and includes, but is not limited to, straight and branched chains such as methyl, ethyl, n-propyl, isopropyl, n-butyl, isobutyl, sec-butyl, t-butyl, n-pentyl, isopentyl, neopentyl, n-hexyl, and isohexyl. Lower alkyl refers to alkyl having 1 to 3 carbon atoms.

Alkanamido, as used herein, refers to the group R—C(=O)—NH— where R is an alkyl group of 1 to 5 carbon atoms.

Alkanoyl, as used herein, refers to the group R—C(=O)— where R is an alkyl group of 1 to 5 carbon atoms.

Alkanoyloxy, as used herein, refers to the group R—C(=O)—O— where R is an alkyl group of 1 to 5 carbon atoms.

Alkanesulfonamido, as used herein, refers to the group R—S(O)$_2$—NH— where R is an alkyl group of 1 to 6 carbon atoms.

Alkanesulfonyl, as used herein, refers to the group R—S(O)$_2$— where R is an alkyl group of 1 to 6 carbon atoms.

Alkoxy, as used herein, refers to the group R—O— where R is an alkyl group of 1 to 6 carbon atoms.

Aryl, as used herein, refers to an aromatic 5- to 7-membered monocarbocyclic ring such as phenyl. Heteroaryl means an aromatic 5- to 7-membered carbon containing monocyclic ring having one to two heteroatoms which independently may be nitrogen, oxygen or sulfur. Groups containing aryl or heteroaryl moieties may optionally be substituted as defined herein or unsubstituted.

Aroyl, as used herein, refers to the group Ar—C(=O)— where Ar is aryl as defined above. For example, a $C_6$ to $C_8$ aroyl moiety refers to the group Ar—C(=O)— where Ar is an aromatic 5 to 7 membered carbocylic ring.

Alkylaryl, as used herein refers to the group —R—Ar where Ar is aryl as defined above and R is an alkyl moiety having 1 to 6, preferably 1 to 4, and more preferably 1 to 3 carbon atoms. Examples of alkylaryl groups include benzyl, phenethyl, 3-phenylpropyl, and 4-phenyl butyl. Alkylheteroaryl, as used herein, refers to the group —R-hetAr where hetAr is heteroaryl as defined above and R is an alkyl moiety having 1 to 6, preferably 1 to 4, and more preferably 1 to 3 carbon atoms.

Carboxamido, as used herein, refers to the group NH$_2$—C(=O)—.

Carboalkoxy, as used herein, refers to the group R—O—C(=O)— where R is an alkyl group of 1 to 5 carbon atoms.

Carboarylalkoxy as used herein, refers to the group Ar—Ra—O—C(=O)— where Ar is aryl as defined above, and Ra is a lower alkyl group of 1 to 3 carbon atoms. Preferably, Ar is phenyl and Ra is methylene to form a benzyl moiety.

Halogen (or halo) as used herein refers to chlorine, bromine, fluorine and iodine.

Pharmaceutically acceptable salts, including mono- and bi- salts, are those derived from such organic and inorganic acids such as, but not limited to acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of compounds of Formula I include:
4,5,6,7,9,9a10,11,12,12a-decahydrocyclopenta[c][1,4]diazepino[6,7,1-ij]quinoline;
4,5,6,7,9a,10,11,12,13,13a-decahydro-9H-[1,4]diazepino[6,7,1-de]phenanthridine hydrochloride;
4,5,6,7,9,9a,10,11,12,13,14,14a-dodecahydrocyclohepta[c][1,4]diazepino[6,7,1-ij]quinoline;
2-bromo-4,5,6,7,9,9a,10,11,12,12a-decahydrocyclopenta[c][1,4]diazepino[6,7,1-ij]quinoline hydrochloride
2-bromo-4,5,6,7,9,9a,10,11,12,13,14,14a-dodecahydrocyclohepta[c][1,4]diazepino[6,7,1-ij]quinoline hydrochloride;
2-chloro-4,5,6,7,9,9a,10,11,12,12a-decahydrocyclopenta[c][1,4]diazepino[6,7,1-ij]quinoline hydrochloride;
2-chloro-4,5,6,7,9,9a,10,11,12,13,14,14a-dodecahydrocyclohepta[c][1,4]diazepino[6,7,1-ij]quinoline hydrochloride;
2-phenyl-4,5,6,7,9,9a,10,11,12,12a-decahydrocyclopenta[c][1,4]diazepino[6,7,1-ij]quinoline hydrochloride;
2-methoxy-4,5,6,7,9,9a,10,11,12,12a-decahydrocyclopenta[c][1,4]diazepino[6,7,1-ij]quinoline hydrochloride;
1-fluoro-4,5,6,7,9,9a,10,11,12,12a-decahydrocyclopenta[c][1,4]diazepino[6,7,1-ij]quinoline hydrochloride;
1-fluoro-4,5,6,7,9,9a,10,11,12,13,14,14a-dodecahydrocyclohepta[c][1,4]diazepino[6,7,1-ij]quinoline hydrochloride;
1-(trifluoromethyl)-4,5,6,7,9,9a,10,11,12,12a-decahydrocyclopenta[c][1,4]diazepino[6,7,1-ij]quinoline hydrochloride;
1-fluoro-2-methoxy-4,5,6,7,9,9a,10,11,12,12a-decahydrocyclopenta[c][1,4]diazepino[6,7,1-ij]quinoline hydrochloride;
1-fluoro-2-methoxy-4,5,6,7,9,9a,10,11,12,13,14,14a-dodecahydrocyclo-hepta[c][1,4]diazepino[6,7,1-ij]quinoline hydrochloride;
and pharmaceutically acceptable salts thereof.

Additional specific examples of compounds of Formula I include:
5-acetyl-4,5,6,7,9,9a,10,11,12,12a-decahydrocyclopenta[c][1,4]diazepino[6,7,1-ij]quinoline;
benzyl 6,7,9a,10,11,12,13,13a-octahydro-9H-[1,4]diazepino[6,7,1-de]phenanthridine-5(4H)-carboxylate;
5-acetyl-4,5,6,7,9,9a,10,11,12,13,14,14a-dodecahydrocyclohepta[c][1,4]diazepino[6,7,1-ij]quinoline;
benzyl 2-bromo-6,7,9,9a,10,11,12,12a-octahydrocyclopenta[c][1,4]diazepino[6,7,1-ij]quinoline-5(4H)-carboxylate;
benzyl 2-bromo-6,7,9,9a,10,11,12,13,14,14a-decahydrocyclohepta[c][1,4]diazepino[6,7,1-ij]quinoline-5(4H)-carboxylate;
benzyl 2-chloro-6,7,9,9a,10,11,12,12a-octahydrocyclopenta[c][1,4]diazepino[6,7,1-ij]quinoline-5(4H)-carboxylate;
benzyl 2-chloro-6,7,9,9a,10,11,12,13,14,14a-decahydrocyclohepta[c][1,4]diazepino[6,7,1-ij]quinoline-5(4H)-carboxylate;

benzyl 2-phenyl-6,7,9,9a,10,11,12,12a-octahydrocyclopenta[c][1,4]diazepino[6,7,1-ij]quinoline-5(4H)-carboxylate;

benzyl 2-methoxy-6,7,9,9a,10,11,12,12a-octahydrocyclopenta[c][1,4]diazepino[6,7,1-ij]quinoline-5(4H)-carboxylate;

benzyl 1-fluoro-6,7,9,9a,10,11,12,12a-octahydrocyclopenta[c][1,4]diazepino[6,7,1-ij]quinoline-5(4H)-carboxylate;

benzyl 1-fluoro-6,7,9,9a,10,11,12,13,14,14a-decahydrocyclohepta[c][1,4]diazepino[6,7,1-ij]quinoline-5(4H)-carboxylate;

benzyl 1-(trifluoromethyl)-6,7,9,9a,10,11,12,12a-octahydrocyclopenta[c][1,4]diazepino[6,7,1-ij]quinoline-5(4H)-carboxylate;

benzyl 1-fluoro-2-methoxy-6,7,9,9a,10,11,12,12a-octahydrocyclopenta[c][1,4]diazepino[6,7,1-ij]quinoline-5(4H)-carboxylate benzyl 1-fluoro-2-methoxy-6,7,9,9a,10,11,12,13,14,14a-decahydrocyclo-hepta[c][1,4]diazepino[6,7,1-ij]quinoline-5(4H)-carboxylate;

and pharmaceutically acceptable salts thereof.

Specific examples also include substantially enantiomerically pure compounds of the foregoing including:

(−)-5-acetyl-4,5,6,7,9,9a,10,11,12,12a-decahydrocyclopenta[c][1,4]diazepino[6,7,1-ij]quinoline, (+)-5-acetyl-4,5,6,7,9,9a,10,11,12,12a-decahydrocyclopenta[c][1,4]diazepino[6,7,1-ij]quinoline;

(9aR,14aS)-5-acetyl-4,5,6,7,9,9a,10,11,12,13,14,14a-dodecahydrocyclo-hepta[c][1,4]diazepino[6,7,1-ij]quinoline (9aS,14aR)-5-acetyl-4,5,6,7,9,9a,10,11,12,13,14,14a-dodecahydrocyclo-hepta[c][1,4]diazepino[6,7,1 -ij]quinoline (−)-4,5,6,7,9,9a10,11,12,12a-decahydrocyclopenta[c][1,4]diazepino[6,7,1 -ij]quinoline;

(9aR,14aS)-4,5,6,7,9,9a,10,11,12,13,14,14a-dodecahydrocyclohepta[c][1,4]diazepino[6,7,1-ij]quinoline hydrochloride;

(9aS,14aR)-4,5,6,7,9,9a,10,11,12,13,14,14a-dodecahydrocyclohepta[c][1,4]diazepino[6,7,1-ij]quinoline hydrochloride;

and pharmaceutically acceptable salts thereof.

The compounds of this invention can be prepared according to the following schemes from commercially available starting materials or starting materials which can be prepared using literature procedures. Variables used are as defined for Formula I, unless otherwise noted.

In Scheme I below, a substituted or unsubstituted benzodiazepinedione is reduced with a reducing agent, such as lithium aluminum hydride or a borane-tetrahydrofuran complex, to give a substituted or unsubstituted benzodiazepine. The basic nitrogen of the benzodiazepine is acylated with an acylating reagent, such as an acid anhydride or a chloroformate, in the presence of a base, such as triethylamine or hunigs base, in an organic solvent, such as ether or methylene chloride, to give intermediate I. Intermediate I is allowed to react with a formaldehyde equivalent, such as a solution of aqueous formaldehyde or dimethoxymethane, in the presence of a Lewis acid such as boron trifluoride, and a dienophile such as cyclopentene or an alkyne to give the cycloadduct II. The cycloadduct is then treated under basic conditions, such as KOH in polar solvents like water and ethanol, to give III. Alternatively, II can be subjected to catalytic hydrogenolysis, such as palladium on charcoal to yield III. Compounds II, when the double bond is absent are racemic mixtures which can be resolved using chiral HPLC to give separated enantiomers which can then be treated with an inorganic base, such as KOH in a polar solvent, such as water or methanol at elevated temperatures, such as 50–100° C., to remove the acyl group giving enantiomers IV and V, which are products of this invention. Enantiomers IV and V can also be obtained by chiral salt resolution of racemic III using a resolving agent, such as benzoyltartaric acid, in an organic solvent, such as an alcohol.

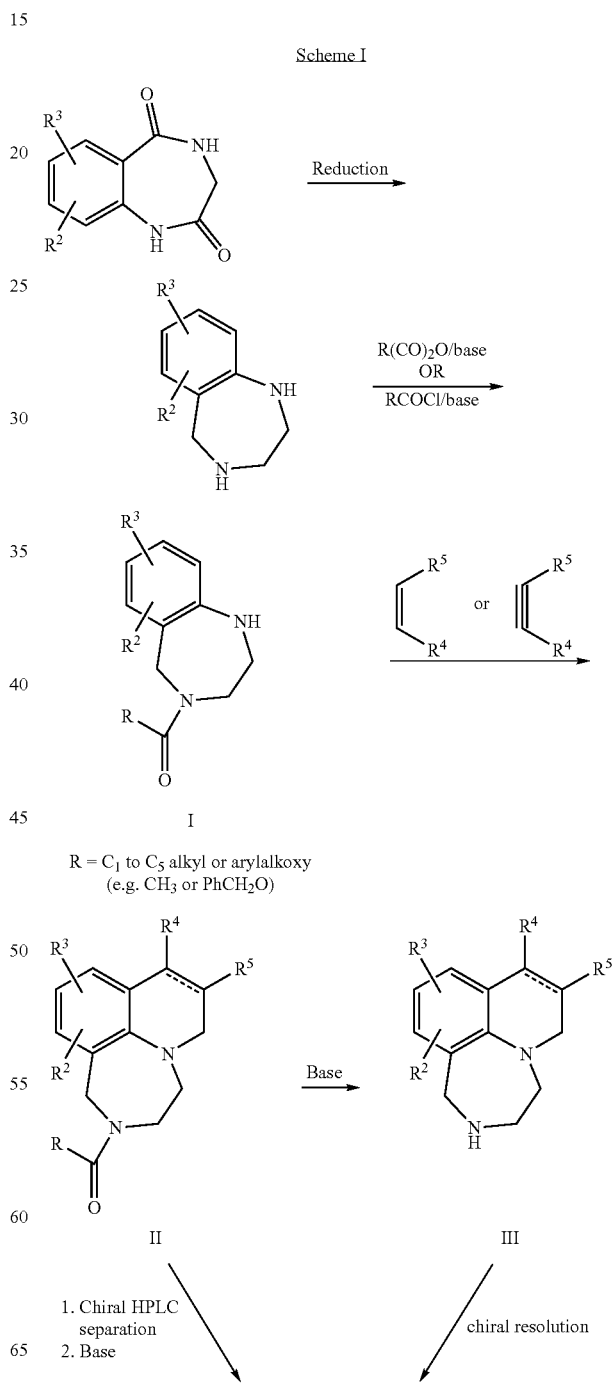

-continued

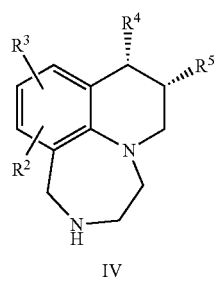

IV

+

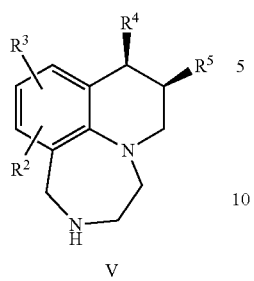

V

Compounds of the present invention where n is 2 can be prepared according to Scheme I above, except that the starting compound in Scheme I is replaced by compound XXI below and is subject to the same chemistry.

XXI

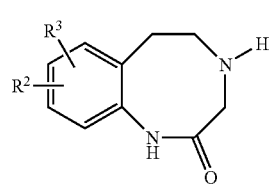

This starting compound for where n is 2 in Formula I can be prepared according to the following reaction Scheme Ia:

Scheme Ia

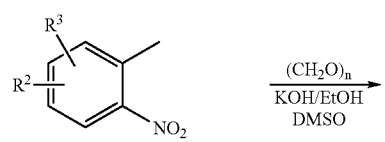

XIV

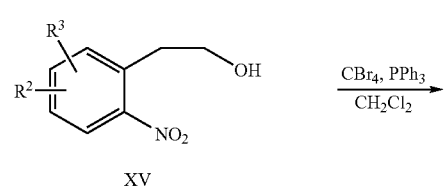

XV

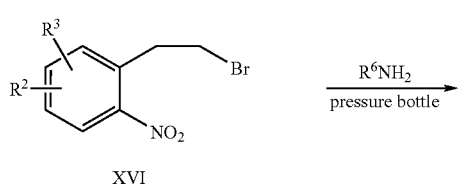

XVI

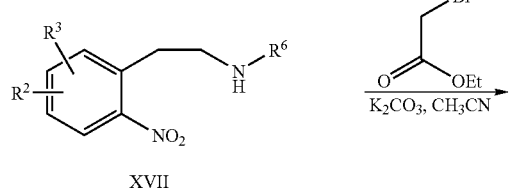

XVII

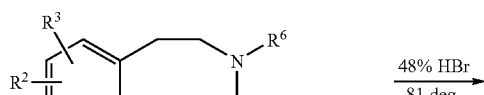

XVIII

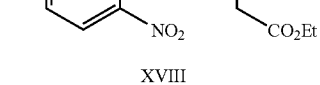

XIX

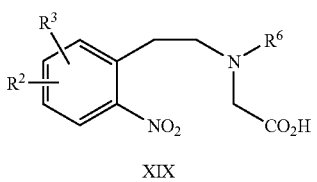

XX

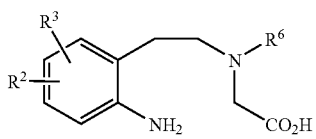

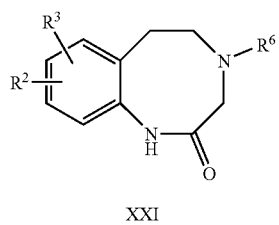

XXI

In Scheme Ia, the appropriately substituted nitrotoluene XIV is treated with paraformaldehyde in the presence of a suitable base such a potassium hydroxide in a solvent such as DMSO-ethanol to give the phenylethanol XV, which is converted to the bromide XVI using standard procedures, such as treatment with carbon tetrabromide and triphenylphosphine in methylene chloride. The bromide is converted to the phenethylamine XVII by treatment with ammonia ($R^6$ is hydrogen) at elevated temperature in a high pressure vessel and the phenethylamine alkylated with ethyl bromoacetate in the presence of a base such as potassium carbonate in a suitable solvent such as acetonitrile or dimethylformamide. The resulting amino ester XVIII is hydrolyzed to the acid by treatment with hydrobromic acid to give the amino acid XIX. Following reduction of the aromatic nitro group with hydrogen in the presence of a suitable catalyst such as platinum on sulfided carbon or palladium on carbon, cyclization to 3,4,5,6-tetrahydro-1H-benzo[e][1,4]diazocin-2-one XXI is effected by treatment with a coupling reagent such as dicyclohexylcarbodiimide in a solvent such as pyridine.

Alternatively, the compounds of the present invention can also be prepared using the synthetic route shown in Scheme II.

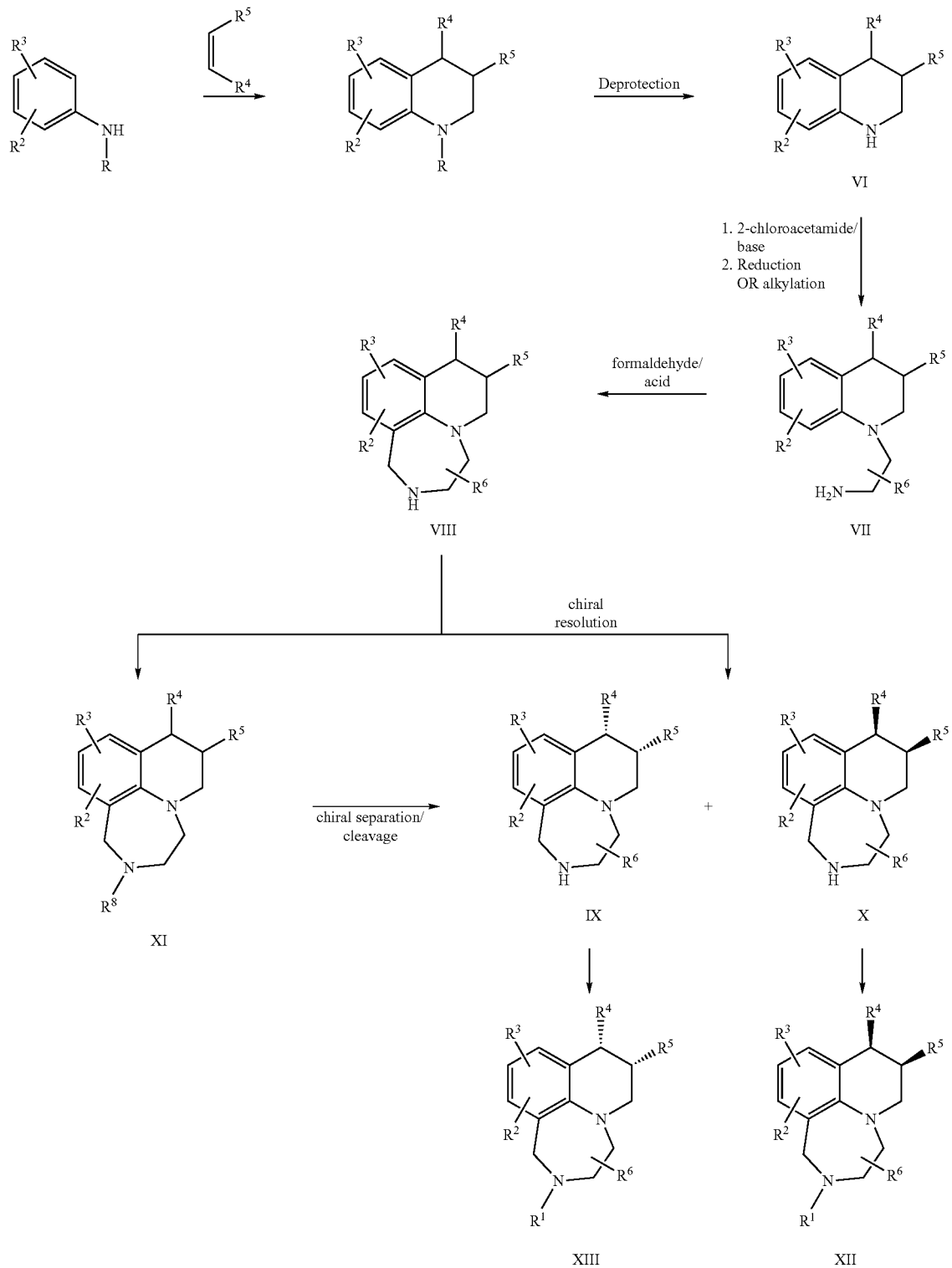

Scheme II

Anilines or appropriately N-substituted anilines such as N-benzyl aniline can be reacted with a formaldehyde equivalent, such as a solution of aqueous formaldehyde or dimethoxymethane, in the presence of a Lewis acid such as boron trifluoride, and a dienophile such as cyclopentene to give the cycloadduct. Wherever applicable, the R group on the nitrogen is subsequently deprotected to give intermediates VI. Intermediate VI can subsequently be alkylated, for instance with 2-chloroethyl amine under phase transfer conditions to yield VII. Alternatively, the side chain can also be installed via a two step procedure of alkylation with 2-chloroacetamide followed by reduction. VII is then subject to a pictet-spengler cyclization conditions with formaldehyde and a protic acid such as trifluoroacetic acid to yield VIII.

VII can be resolved subsequently into its pure enantiomers by a chiral resolution to give compounds IX and X. Alternatively, VIII can be derivatised appropriately to give XI which can be separated by chiral chromatography and then subject to cleavage to give IX and X. These compounds can then be derivatised, for example, by alkylation, to give compounds XII and XIII, where $R^1$ is a $C_1$ to $C_6$ alkyl.

The compounds of this invention are agonists and partial agonists at the 2c subtype of brain serotonin receptors and are thus of interest for the treatment of mental disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorders with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders such as depressive disorders or bipolar disorders often accompany psychotic disorders such as schizophrenia. A more complete description of the aforementioned mental disorders can be found in the Diagnostic and Statistical Manual of Mental Disorders, 4$^{th}$ edition, Washington, D.C., American Psychiatric Association (1994).

The compounds of the present invention are also of interest for the treatment of epilepsy; migraines; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of the present invention can also be used to treat central nervous system deficiencies associated, for example, with trauma, stroke, and spinal cord injuries. The compounds of the present invention can therefore be used to improve or inhibit further degradation of central nervous system activity during or following the malady or trauma in question. Included in these improvements are maintenance or improvement in motor and motility skills, control, coordination and strength.

The ability of the compounds of this invention to act as $5HT_{2C}$ agonists and partial agonists was established using several standard pharmacological test procedures; the procedures used and results obtained are provided below. In the test procedures, 5-HT stands for 5-hydroxytryptamine, mCPP stands for meta-chlorophenylpiperazine, and DOI stands for 1-(2,5-dimethoxy-4-iodophenyl)isopropylamine.

$5HT_{2C}$ Receptor Binding Test Procedures

To evaluate high affinity for the $5HT_{2C}$ receptor, a CHO (Chinese Hamster Ovary) cell line transfected with the cDNA expressing the human 5-hydroxytryptamine$_{2C}$ (h5HT$_{2C}$) receptor was maintained in DMEM (Dulbecco's Modified Eagle Media) supplied with fetal calf serum, glutamine, and the markers: guaninephosphoribosyl transferase (GTP) and hypoxanthinethymidine (HT). The cells were allowed to grow to confluence in large culture dishes with intermediate changes of media and splitting. Upon reaching confluence, the cells were harvested by scraping. The harvested cells were suspended in half volume of fresh physiological phosphate buffered saline (PBS) solution and centrifuged at low speed (900×g). This operation was repeated once more. The collected cells were then homogenized with a polytron at setting #7 for 15 sec in ten volumes of 50 mM Tris.HCl, pH 7.4 and 0.5 mM EDTA. The homogenate was centrifuged at 900×g for 15 min to remove nuclear particles and other cell debris. The pellet was discarded and the supernatant fluid recentrifuged at 40,000×g for 30 min. The resulting pellet was resuspended in a small volume of Tris.HCl buffer and the tissue protein content was determined in aliquots of 10–25 microliter (µl) volumes. Bovine Serum Albumin (BSA) was used as the standard in the protein determination by the method of (Lowry et al, J. Biol. Chem., 193: 265,1951). The volume of the suspended cell membranes was adjusted with 50 mM Tris.HCl buffer containing: 0.1% ascorbic acid, 10 mM pargyline and 4 mM $CaCl_2$ to give a tissue protein concentration of 1–2 mg per ml of suspension. The preparation membrane suspension (many times concentrated) was aliquoted in 1 ml volumes and stored at −70 C. until used in subsequent binding experiments.

Binding measurements were performed in a 96 well microtiter plate format, in a total volume of 200 µl. To each well was added: 60 µl of incubation buffer made in 50 mM Tris.HCl buffer, pH 7.4 and containing 4 mM $CaCl_2$; 20 µl of [$^{125}$I] DOI (S.A., 2200 Ci/mmol, NEN Life Science).

The dissociation constant, KD of [$^{125}$I] DOI at the human serotonin $5HT_{2C}$ receptor was 0.4 nM by saturation binding with increasing concentrations of [$^{125}$I] DOI. The reaction was initiated by the final addition of 100.0 µl of tissue suspension containing 50 µg of receptor protein. Nonspecific binding is measured in the presence of 1 µM unlabeled DOI added in 20.0 µl volume. Test compounds were added in 20.0 ml. The mixture was incubated at room temperature for 60 min. The incubation was stopped by rapid filtration. The bound ligand-receptor complex was filtered off on a 96 well unifilter with a Packard® Filtermate 196 Harvester. The bound complex caught on the filter disk was dried in a vacuum oven heated to 60° C. and the radioactivity measured by liquid scintillation with 40 µl Microscint-20 scintillant in a Packard TopCount® equipped with six (6) photomultiplier detectors.

Specific binding is defined as the total radioactivity bound less the amount bound in the presence of 1 µM unlabeled DOI. Binding in the presence of varying concentrations of test drugs is expressed as percent of specific binding in the absence of drug. These results are then plotted as log % bound vs log concentration of test drug. Non linear regression analysis of data points yields both the IC50 and the Ki values of test compounds with 95% confidence limits. Alternatively, a linear regression line of decline of data points is plotted, from which the IC50 value can be read off the curve and the Ki value determined by solving the following equation:

$$Ki = \frac{IC50}{1 + L/KD}$$

where L is the concentration of the radioactive ligand used and the KD is the dissociation constant of the ligand for the receptor, both expressed in nM.

The following $K_i$'s (95% confidence interval) are provided for various reference compounds:

| | |
|---|---|
| Ritanserin | 2.0 (1.3–3.1) nM |
| Ketanserin | 94.8 (70.7–127.0) nM |
| Mianserin | 2.7 (1.9–3.8) nM |
| Clozapine | 23.2 (16.0–34.0) nM |
| Methiothepin | 4.6 (4.0–6.0) nM |
| Methysergide | 6.3 (4.6–8.6) nM |
| Loxapine | 33.0 (24.0–47.0) nM |
| mCPP | 6.5 (4.8–9.0) nM |
| DOI | 6.2 (4.9–8.0) nM |

Calcium Mobilization in Response to 5-HT$_{2C}$ Receptor Agonists

CHO cells stably expressing the human 5-HT$_{2C}$ receptor were cultured in Dulbecco's modified Eagle's medium (DMEM) supplemented with 10% fetal bovine serum and non-essential amino acids. Cells were plated at a density of 40K cells/well in 96-well clear-bottom black-wall plates 24 hr prior to the evaluation of 5-HT$_{2C}$ receptor stimulated calcium mobilization. For calcium studies cells were loaded with the calcium indicator dye Fluo-3-AM in Hank's buffered saline (HBS) for 60 minutes at 37° C. Cells were washed with HBS at room temperature and transferred to the fluorometric imaging plate reader (FLIPR, Molecular Devices, Sunnyvale, Calif.) for acquisition of calcium images. Excitation at 488 nm was achieved with an Argon ion laser and a 510–560 nm emission filter was used. Fluorescence images and relative intensities were captured at 1 second intervals and cells were stimulated by addition of agonist after 10 baseline measurements using the internal fluidics module of the FLIPR. An increase in fluorescence counts corresponds to an increase in intracellular calcium.

For the evaluation of agonist pharmacology the calcium changes in response to different concentrations of agonist were determined using a maximum minus minimum calculation of the raw fluorescence count data. Calcium changes were then expressed as a percentage of the response observed with a maximally effective concentration of 5-HT and EC50 values were estimated by non-linear regression analysis of the log-concentration % maximum 5-HT response curves using the 4-parameter logistic function.

The following EC$_{50}$'s and IC$_{50}$'s are provided for various reference compounds:

| | | |
|---|---|---|
| 5-HT | EC50 | 0.5 nM |
| DOI | EC50 | 0.5 nM |
| mCPP | EC50 | 5.4 nM |

The results of the standard experimental test procedures described in the preceding paragraphs were as follows:

| | 5-HT$_{2C}$ Affinity (DOI/Agonist binding) KI (nM) | 5-HT$_{2C}$ Function | |
|---|---|---|---|
| Compound | | EC$_{50}$ (nM) | Emax (%) (5-HT, 100%) |
| Example 4 | 3 | 8 | 100 |
| Example 6 | 24 | 65 | 60 |
| Example 8 | 13 | 261 | 70 |
| Example 10 | 56 | | |
| Example 12 | 117 | | |
| Example 16 | 2299 | | |
| Example 20 | 373 | | |
| Example 22 | 88 | | |
| Example 24 | 199 | | |
| Example 26 | 20 | | |
| Example 28 | 169 | | |
| Example 30 | 59 | | |
| Example 32 | 223 | | |
| Example 34 | 249 | | |

The compounds of this invention thus have affinity for and agonist or partial agonist activity at brain serotonin receptors. They are therefore of interest for the treatment of such CNS disorders, including psychotic disorders such as schizophrenia including paranoid type, disorganized type, catatonic type, and undifferentiated type, schizophreniform disorder, schizoaffective disorder, delusional disorder, substance-induced psychotic disorder, and psychotic disorder not otherwise specified; L-DOPA-induced psychosis; psychosis associated with Alzheimer's dementia; psychosis associated with Parkinson's disease; psychosis associated with Lewy body disease; bipolar disorders such as bipolar I disorder, bipolar II disorder, and cyclothymic disorder; depressive disorders such as major depressive disorder, dysthymic disorder, substance-induced mood disorder, and depressive disorder not otherwise specified; mood episodes such as major depressive episode, manic episode, mixed episode, and hypomanic episode; anxiety disorders such as panic attack, agoraphobia, panic disorder, specific phobia, social phobia, obsessive compulsive disorder, posttraumatic stress disorder, acute stress disorder, generalized anxiety disorder, separation anxiety disorder, substance-induced anxiety disorder, and anxiety disorder not otherwise specified; adjustment disorders such as adjustment disorders with anxiety and/or depressed mood; intellectual deficit disorders such as dementia, Alzheimer's disease, and memory deficit; eating disorders (e.g., hyperphagia, bulimia or anorexia nervosa) and combinations of these mental disorders that may be present in a mammal. For example, mood disorders or episodes, such as depressive disorders or episodes often accompany psychotic disorders such as schizophrenia. A more complete description of the aforementioned mental disorders can be found in the Diagnostic and Statistical Manual of Mental Disorders, 4th edition, Washington, D.C., American Psychiatric Association (1994).

The compounds of the present invention are also of interest for the treatment of epilepsy; migraines; sexual dysfunction; sleep disorders; gastrointestinal disorders, such as malfunction of gastrointestinal motility; and obesity, with its consequent comorbidities including Type II diabetes, cardiovascular disease, hypertension, hyperlipidemia, stroke, osteoarthritis, sleep apnea, gall bladder disease, gout, some cancers, some infertility, and early mortality. The compounds of the present invention can also be used to treat central nervous system deficiencies associated, for example, with trauma, stroke, spinal cord injuries. The compounds of the present invention can therefore be used to improve or inhibit further degradation of central nervous system activity during or following the malady or trauma in question. Included in these improvements are maintenance or improvement in motor and motility skills, control, coordination and strength.

Thus the present invention provides methods of treating each of the maladies listed above in a mammal, preferably in a human, the methods comprising providing a therapeutically effective amount of a compound of this invention to the mammal in need thereof. By "treating", as used herein, it is meant partially or completely alleviating, inhibiting, preventing, ameliorating and/or relieving the disorder. For example, "treating" as used herein includes partially or completely alleviating, inhibiting or relieving the condition in question. "Mammals" as used herein refers to warm blooded vertebrate animals, such as humans. "Provide", as used herein, means either directly administering a compound or composition of the present invention, or administering a prodrug derivative or analog which will form an equivalent amount of the active compound or substance within the body.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers, the proportion of which is determined by the solubility and chemical nature of the compound, chosen route of administration and standard pharmacological practice. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be administered by, for example, intramuscular, intraperitoneal or subcutaneous injection. Sterile solutions can also be administered intravenously. Oral administration may be either liquid or solid composition form.

The compounds of this invention may be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage requirements vary with the particular compositions employed, the route of administration, the severity of the symptoms presented and the particular subject being treated. Based on the results obtained in the standard pharmacological test procedures, projected daily dosages of active compound would be 0.02 µg/kg–750 µg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated.

The present invention includes prodrugs of compounds of Formula I. Prodrug, as used herein, means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Delivery Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

EXAMPLES

The following provides the preparation of compounds representative of this invention.

Example 1

5-acetyl-4,5,6,7,9,9a,10,11,12,12a-decahydrocyclopenta[c][1,4diazepino[6,7,1-ij]quinoline Dimethoxymethane (34.9 mL, 394 mmol) was dissolved in methylene chloride (800 mL) and cooled to 0° C. in a ice bath. To this solution, boron trifluoride etherate (18.3 mL, 144 mmol) was added and the reaction was stirred for 30 minutes. Subsequently, a solution of 4-Acetyl-2,3,4,5-tetrahydro-1H-1,4-benzodiazepine (25 g, 131 mmol) in methylene chloride (500 mL) was added to the reaction through an addition funnel over several hours. During the course of this addition, cyclopentene (23.1 mL, 263 mmol) was added to the reaction. The reaction was allowed to warm to room temperature overnight. Additional portions of the dimethoxymethane, boron trifluoride etherate and cyclopentene were added as necessary to facilitate greater conversion. The reaction was neutralized with NaOH and extracted with methylene chloride and the organic layer was washed with saturated brine solution. After drying with MgSO$_4$, the solvent was evaporated in vacuo and the product was purified by flash chromatography (silica gel, ethyl acetate:hexanes 55:45 with 1% triethylamine) to provide 7.4 grams of the title compound.
MS (ESI) m/z 271 ([M+H]$^+$).

Example 2

(−)-5-acetyl-4,5,6,7,9,9a,10,11,12,12a-decahydrocyclopenta[c][1,4]diazepino[6,7,1-ij]quinoline The compound of example 1 was separated by HPLC using a Chiralcel OD or Chiralpak AS column using 9:1 hexane:isopropanol at 0.8 mL/min. The first enantiomer (Example 2) eluted at 18.9 min and the second enantiomer eluted at 20.9 min.
Peak 1 was obtained as colorless semisolid and identified as an enantiomer of 5-acetyl-4,5,6,7,9,9a10,11,12,12a-decahydrocyclopenta[c][1,4]diazepino[6,7,1-ij]quinoline.
$[\alpha]^{25}_D$=−191.2 (CHCl$_3$); MS (ESI) m/z 271 ([M+H]$^+$).

Example 3

(+)-5-acetyl-4,5,6,7,9,9a,10,11,12,12a-decahydrocyclopenta[c][1,4]diazepino[6,7,1-ij]quinoline The compound of example 1 was separated by HPLC using a Chiralcel OD or Chiralpak AS column using 9:1 hexane:isopropanol at 0.8 mL/min. The first enantiomer (Example 2) eluted at 18.9 min and the second enantiomer eluted at 20.9 min.
Peak 2 was obtained as colorless semisolid and identified as an enantiomer of 5-acetyl-4,5,6,7,9,9a10,11,12,12a-decahydrocyclopenta[c][1,4]diazepino[6,7,1-ij]quinoline.
$[\alpha]^{25}_D$=+165.1 (CHCl$_3$); MS (ESI) m/z 271 ([M+H]$^+$).

Example 4

(−)-4,5,6,7,9,9a10,11,12,12a-decahydrocyclopenta[c][1,4]diazepino[6,7,1-ij]quinoline The compound of example 2 (440 mgs, 1.6 mmol) was dissolved in methanol (4 mL) and water (2 mL) and KOH (900 mgs, 16 mmol) was added. The reaction was heated to reflux for 15 hours and the methanol was removed in vacuo. The reaction was diluted with ethyl acetate and water and extracted. After drying with MgSO$_4$, the solvent was evaporated in vacuo and the product was purified by flash chromatography (silica gel, ethyl acetate:methanol containg 2.0M ammonia, 98:2). This compound was isolated as the hydrochloride salt.
$[\alpha]^{25}_D$=−274.63 (CHCl$_3$); MS(ESI) m/z 229 (([M+H]$^+$).
Elemental Analysis for: $C_{15}H_{20}N_2$.HCl; Theory: C, 68.04; H, 7.99; N, 10.58;
Found: C, 67.92; H, 8.16; N, 10.53.

Intermediate 1

Benzyl 1,2,3,5-tetrahydro-4H-1,4-benzodiazepine-4-carboxylate 2,3,4,5-Tetrahydro-1H benzo[e][1,4]diazepine (5 g, 33.7 mmol) was dissolved in THF (168.5 mL and cooled to 0° C. with an ice bath. Hunig's base (8.81 mL, 50.6 mmol) and benzyl chloroformate (5.30 mL, 37.1 mmol) was added dropwise with stirring. After 7 hours stirring, THF was removed, and water and ethyl ether were added to the flask. The reaction mixture was extracted with diethyl ether (4×), and the combined organic extracts were washed with aqueous sodium bicarbonate (1×) and brine (1×). The organic extracts were then dried with magnesium sulfate, filtered and concentrated to give a yellow oil. Further purification (25:75 ethyl acetate/hexane, then 30:70 ethyl acetate/hexane) yielded 7.9 g of desired product (83%).
$^1$H NMR (CDCl$_3$, 400 MHz): δ 7.34–7.26 (d, 6H); 7.13(t, 1H); 6.87 (m, 2H); 5.09 (s, 2H); 4.47 (d, 2H); 3.74 (s, 2H); 3.17 (d, 2H); 1.58 (bs, 1H—NH)
Mass Spec: Calculated: 282.34; Found: 283.46 [M+H]$^+$ Example 5

Benzyl 6,7,9a,10,11,12,13,13a-octahydro-9H-[1,4]diazepino[6,7,1-de]phenanthridine-5(4H)-carboxylate Intermediate 1 (5 g, 17.7 mmol) was dissolved in methylene chloride (90 mL). Dimethoxymethane (4.7 mL, 53.1 mmol) and cyclohexene (3.6 mL, 35.4 mmol) were added at room temperature. The reaction flask was then cooled to 0° C. Boron trifluoride diethyl etherate (2.5 mL, 19.5 mmol) was added drop wise over 5 minutes. The reaction was warmed to room temperature gradually overnight. After 20 hours, the reaction was heated to 40° C. At 36 hours, another portion of boron trifluoride diethyl etherate, dimethoxymethane and cyclohexene (9.74 mmol, 20.6 mmol and 17.7 mmol respectively) were added. After a total of 62 hours, the reaction was cooled to room temperature. 1N NaOH was added to the flask and stirred for 30 minutes. The pH was checked to make sure it was basic, then the contents of the flask were transferred to a separatory funnel and extracted with methylene chloride (3×). The combined extracts were washed with brine (1×), dried with magnesium sulfate, filtered and concentrated to give a golden oil. Further purification (10% ethyl acetate/hexane+0.1% TEA– 15% ethyl acetate/hexane+0.1% TEA) yielded the desired product.

$^1$H NMR (CDCl$_3$, 400 MHz): δ 7.38–7.28 (m, 5H); 7.02–6.96 (3 d, 2H); 6.82–6.7 (m, 1H); 5.13–5.09 (m, 1H); 4.52 (d, 1H); 4.39 (2 d, 1H); 3.48 (t, 1H); 3.17 (d, 2H); 2.99 (d, 1H); 2.75 (m, 1H); 2.18 (bm, 1H); 1.82 (2 d, 1H); 1.73–1.50 (m, 6H); 1.43–1.36 (m, 2H)

Mass Spec: Calculated: 376.50; Found: 377.13 [M+H]$^+$.

Example 6

4,5,6,7,9a,10,11,12,13,13a-decahydro-9H-[1,4]diazepino[6,7,1-de]phenanthridine hydrochloride The compound from Example 5 (0.200 g, 0.53 mmol) was dissolved in methylene chloride (0.5 mL). Trifluoromethane sulfonic acid (0.0329 mL, 3.72 mmol) and anisole (0.115 mL, 1.06 mmol) were added at 0° C. After 2 hours, another portion of trifluoromethane sulfonic acid (2 eq.) was added. After a total of 4 hours, the reaction was completed. 1 N NaOH was added to quench the reaction (pH=9–10). The contents of the flask were transferred to a separatory funnel with methylene chloride and water, and extracted with methylene chloride (3×). The combined organic extracts were dried with magnesium sulfate, filtered and concentrated to give a brown oil, crude desired product. Further purification (10% ammonia in 2M solution of methanol/ ethyl acetate) yielded 0.067 g of desired product (52%). The free amine product (0.0605 g, 0.249 mmol) was then dissolved in diethyl ether, and a 2M solution of hydrogen chloride (0.137 mL, 0.274 mmol) was added. After 40 minutes, the yellow precipitate was filtered off to give the desired product.

$^1$H NMR (DMSO-d$_6$, 400 MHz): δ 9.64 (bs); 9.24 (bs); 7.06 (2 d, 2H); 6.76 (t, 1H); 4.67 (s,); 4.05 (q, 2H); 3.35–3.12 (m, 5H); 3.01 (2 d, 1H); 2.67 (m, 1H); 2.03 (m, 1H); 1.73–1.18 (m, 8H).

Mass Spec: Calculated: 242.36; Found: 243.15 [M+H]$^+$.

Example 7

5-acetyl-4,5,6,7,9,9a,10,11,12,13,14,14a-dodecahydrocyclohepta[c][1,4]diazepino[6,7,1-ij]quinoline To a round bottom flask was added dimethoxymethane (0.700 mL, 7.89 mmol), which then was cooled to 0° C. Boron trifluoride diethyl etherate (0.366 mL, 2.89 mmol) was then added and stirred for 30 minutes. A solution of benzodiazpene (0.5 g, 2.63 mmol) and methylene chloride (26.2 mL) was added over ten minutes. When the addition was complete, cycloheptene (0.613 mL, 5.25 mmol) was added. After 20 hours, more boron trifluoride diethyl etherate and dimethoxymethane (0.33 mL and 0.232 mL respectively) was added. After a total of about 60 hours, 1N NaOH was added and allowed to stir for 15 minutes. After checking to make sure the aqueous phase was basic, the contents of the reaction flask were transferred to a separatory funnel with methylene chloride. The reaction mixture was extracted with methylene chloride (1×), and the organic layer was washed with brine (1×), dried with magnesium sulfate, filtered and concentrated to give a brown oil. Further purification (65:35 ethyl acetate/hexane +1% TEA) gave the desired product.

$^1$H NMR (DMSO-d$_6$, 400 MHz): δ 7.2–6.67 (ar m, 3H); 4.38 (q, 1H); 4.06–3.98(m, 1H); 3.2–3.16 (m, 2H); 2.91–2.88 (app d, 2H); 2.81–2.74 (m, 2H); 1.97–1.94 2s, 2H); 1.9 (s, 2H); 1.86–1.81 (m, 4H); 1.66–1.63 (m, 2H); 1.52–1.47 (m, 2H); 1.12 (t, 2H).

Mass Spec: Calculated: 298.42; Found: 299.21 [M+H]$^+$.

Example 8

4,5,6,7,9,9a,10,11,12,13,14,14a-dodecahydrocyclohepta[c][1,4]diazepino[6,7,1-ij]quinoline The compound from example 7 (0.5 g, 1.67 mmol) was dissolved in methanol (5 mL). To the mixture was added KOH (0.99 g and 16.7 mmol) and water (5 mL). The reaction mixture was heated to 100° C. and held for 4 hours. Methanol was then added (10 mL) and the mixture was held for an additional 20 hours (16 mL). At 24 hours, KOH (0.47 g, 8.3 mmol) and methanol (16 mL) were added. After 48 hours, the reaction mixture was cooled to room temperature. The methanol was removed, and the reaction mixture was transferred to separatory funnel with methylene chloride and water. The reaction mixture was extracted with methylene chloride (3×). The combined extracts were dried with magnesium sulfate, filtered and concentrated to dryness to give 430 mg of yellow oil. Further purification (20% ammonia (2M solution in ethanol)/ethyl acetate) yielded 0.273 g of desired product (63%).

$^1$H NMR (CDCl$_3$, 400 MHz): δ 7.09 (d, 1H); 6.97 (d split, 1H); 6.83 (t, 1H); 3.98–3.83 (2d, 2H); 2.97 (m, 6H); 2.45–2.12 (m, 3H); 1.92 (m, 1H); 1.73 (m, 2H 1.51 (m, 3H); 1.22 (m,1H); 1.05 (q, 1H).

Mass Spec: Calculated: 256.39; Found: 257.26 [M+H]$^+$.

Example 9

(9aR,14aS)-5-acetyl-4,5,6,7,9,9a,10,11,12,13,14,14a-dodecahydrocyclohepta[cd][1,4]diazepino[6,7,1-ij]quinoline The desired product was obtained after chiral separation of the compound from example 7.

$^1$H NMR (CDCl$_3$, 400 MHz): δ 7.14–6.79 (ar, 3H); 4.40 (q, 1H); 4.17 (m, 1H); 3.40–2.81 (m, 7H); 2.01–1.40 (m, 14H); 1.23–1.00 (q, 3H).

Mass Spec: Calculated: 298.43; Found: 299.2 [M+H]$^+$.

Example 10

(9aR,14aS)-4,5,6,7,9,9a,10,11,12,13,14,14a-dodecahydrocyclohepta[c][1,4]diazepino[6,7,1-ij]quinoline hydrochloride The compound from example 9 (0.695 g, 2.33 mmol) was dissolved in methanol (11 mL). KOH (0.784 g, 14 mmol) and water (11 mL) were added. The mixture was heated to 125° C. for 7.5 hours, then stirred at room temperature overnight. Another portion of KOH (3.7 eq.) was added after the reaction had been running for 29 hours, and the reaction mixture was then heated again. After 48 hours, more KOH was added (3.2 eq) and the reaction mixture was heated for 5 more days. At that point, the reaction mixture was cooled to room temperature and the methanol was removed. The contents of the flask were transferred to a separatory funnel and extracted with methylene chloride (3×). The combined organic layers were dried with magnesium sulfate, filtered and concentrated to give 0.705 g (wet) of yellow oil. Further purification (10–20% ammonia (2M solution of ethanol)/ethyl acetate) yielded 0.423 g of orange oil (71%). The free amine product was dissolved (0.423 g, 1.65 mmol) in diethyl ether. HCl was added in 1M solution of diethyl ether (1.66 mL). After stirring for 30 minutes, the solid was filtered and dried.

$^1$H NMR (DMSO-d$_6$, 400 MHz): δ 9.43 (bs); 8.85 (bs); 7.17 (d, 1H); 7.14 (d, 1H); 6.88 (t, 1H); 4.08 (m, 2H); 3.30 (d, 1H); 3.12 (t, 3H); 2.97 (d, 1H); 2.83 (d & s, 2H); 2.08 (m, 1H); 1.89 (m, 3H); 1.67 (m, 2H); 1.55 (m, 2H); 1.43 (q, 1H); 1.18 (m, 1H); 1.00 (q, 1H).

Mass Spec: Calculated: 256.39; Found: 257.2 [M+H]$^+$.

Optical Rotation: $[\alpha]^{25}_D$=–148.94.

Example 11

(9aS,14aR)-5-acetyl-4,5,6,7,9,9a,10,11,12,13,14, 14a-dodecahydrocyclohepta[c][1,4]diazepino[6,7,1-ij]quinoline The desired product was obtained by chiral separation of the compound from example 7.

$^1$H NMR (CDCl$_3$, 400 MHz): δ 7.16–6.83 (ar, 3H); 4.47 (app q, 2H); 4.20 (m, 1H); 3.39 (t, 1H); 3.13 (m, 1H); 3.05 (m, 1H); 2.91 (t, 3H); 2.84 (t, 3H); 2.02 (s, 1H); 1.93–1.86 (m, 3H); 1.75–1.61 (m, 2H); 1.58–1.4 (m, 4H); 1.20 (q, 1H); 1.03 (q, 1H).

Mass Spec: Calculated: 298.43; Found: 299.2 [M+H]$^+$.

Example 12

(9aS,14aR)-4,5,6,7,9,9a,10,11,12,13,14,14a-dodecahydrocyclohepta[c][1,4]diazepino[6,7,1-ij] quinoline hydrochloride The compound from example 11 (0.702 g, 2.35 mmol) was dissolved in methanol (11 mL). KOH (0.792 g, 14.1 mmol) and water (11 mL) were added to the flask and heated to 125° C. After 8 hours, the reaction was cooled to room temperature. After 14 hours, the reaction mixture was heated. After 7 hours, more methanol (7 mL) and KOH (0.5 g, 8.8 mmol) were added. After 24 hours, more KOH (0.5 g, 8.8 mmol) was added. After 48 hours, the reaction mixture was cooled to room temperature. The methanol was removed, and the contents of the flask were transferred to a separatory funnel with methylene chloride and water and extracted with methylene chloride (3×). The combined extracts were dried with magnesium sulfate, filtered and concentrated to dryness to give 0.430 g of yellow oil. Further purification (20% ammonia (2M solution in ethanol)/ethyl acetate) afforded 0.4625 g of the desired product (77%).

$^1$H NMR (DMSO-d$_6$, 400 MHz): δ 9.25 (bs); 7.14 (d, 1H); 7.10 (d, 1H); 6.83 (t, 1H); 4.03 (q, 2H); 3.36–3.15 (s hidden under water peak, 2H); 3.06 (s, 3H); 2.95 (d, 1H); 2.80 (t &s, 2H); 2.05 (m, 1H); 1.85 (m, 3H); 1.63 (t, 2H); 1.52 (m, 2H); 1.39 (q, 1H); 1.17 (bt, 1H); 0.99 (q, 1H).

Mass Spec: Calculated: 256.39; Found: 257.2 [M+H]$^+$.

Optical Rotation: $[\alpha]^{25}_D$=+123.54 (CDCl$_3$).

Intermediate 2

7-bromo-2,3,4,5-tetrahydro-1H-1,4-benzodiazepine 7-bromo-3,4-dihydro-1H-1,4-benzodiazepine-2,5-dione (11.8 g, 46.2 mmol) was transferred to a round bottom flask. THF (0.57M) was added to the flask to make a slurry. Lithium aluminum hydride in 1M solution of THF (138.8 mmol) was added dropwise. When the addition was completed, the reaction mixture was heated to 63° C. After 19 hours, the reaction mixture was cooled to room temperature and then to 0° C. Water (3 mL) was added to the cooled reaction mixture, and the reaction mixture was stirred for 1 hour. After the 1 hour, 9 mL of 15% NaOH was added and the reaction mixture was stirred for another hour. Water was then added and the resulting precipitate was filtered off. The precipitate was then washed with ethyl acetate several times. The solvent was removed from the filtrate and the filtrate was transferred to a separatory funnel with ethyl acetate. The filtrate was extracted with ethyl acetate (3×). The combined organic extracts were washed with brine (1×), dried with magnesium sulfate, filtered and concentrated to give a yellow solid. Further purification (1% TEA/Ethyl acetate to start, then switched to 20% ammonia (2M solution in methanol)/ethyl acetate, then 100% methylene chloride) yielded the desired product.

$^1$H NMR (CDCl$_3$, 400 MHz): δ 7.2(s,1H); 7.1 (dd, J=4, 8 Hz, 1H); 6.6(d, J=8 Hz, 1H); 3.8 (s, 2H); 3.0 (dt, J=8 Hz, 4H).

Mass Spec: Calculated: 227.10; Found: 226.96 [M+H]$^+$

Intermediate 3

Benzyl 7-bromo-1,2,3,5-tetrahydro-4H-1,4-benzodiazepine-4-carboxylate

Intermediate 2 (4.5 g, 19.8 mmol) was dissolved in THF (0.2M) and cooled to 0° C. Hunig's Base (30.0 mmol) was added to the solution of Intermediate 2. Over 10 minutes, benzyl chloroformate (21.8 mmol) was added dropwise. The reaction mixture was then warmed to room temperature gradually and held for 21 hours. After 21 hours, THF was removed, and the reaction mixture was dissolved in diethyl ether and water, and transferred to a separatory funnel. The reaction mixture was extracted with diethyl ether (3×). The combined organic extracts were washed with aqueous sodium bicarbonate (1×) and brine (1×). The organic layer was then dried with magnesium sulfate, filtered and concentrated to give a yellow solid. Further purification (2–5% ethyl acetate/methylene chloride) resulted in 5.4 g of a white solid, the desired product (75%).

$^1$H NMR (CDCl$_3$, 400 MHz): δ7.40–7.16 (m, 7H); 6.6 (app t, 1H); 5.0 (s, 2H); 4.39 (minor rotomer s, 2H); 4.33 (major rotomer s, 2H); 3.7(dt, 2H); 3.1(dt, 2H)

Mass Spec: Calculated: 361.24; Found: 362.98 [M+H]$^+$

Example 13

Benzyl 2-bromo-6,7,9,9a,10,11,12,12a-octahydrocyclopenta[c][1,4]diazepino[6,7,1-ij]quinoline-5(4H)-carboxylate Intermediate 3 (1 g, 2.77 mmol) was dissolved in methylene chloride (15 mL). Dimethoxymethane (0.735 mL, 8.3 mmol) and cyclopentene (0.487 mL, 5.53 mmol) were added to the Intermediate 3 solution and the reaction mixture was cooled to 0° C. Boron trifluoride diethyl etherate (0.386 mL, 3.05 mmol) was then added dropwise. The reaction mixture was then warmed to room temperature gradually and held at room temperature for 18 hours. After 18 hours, the reaction mixture was cooled to 0° C. Additional dimethoxymethane (4.15 mmol), cyclopentene (2.77 mmol) and boron trifluoride diethyl etherate (1.52 mmol) were then added the reaction mixture was allowed to warm to room temperature overnight. After a total of 48 hours (from start to completion) 1N NaOH (25 mL) was added to the reaction mixture until the pH of the mixture was basic. The mixture was transferred to a separatory funnel with methylene chloride and was extracted with methylene chloride (3×). The combined organic layers were washed with brine (1×), dried with magnesium sulfate, filtered and concentrated to give an oil. Further purification (Methylene chloride+1% TEA) afforded 0.228 g of the final compound (20%).

$^1$H NMR (DMSO-d$_6$, 400 MHz): δ 5.08–4.97 (m, 2H); 4.59–4.54 (t, 1H); 4.21–4.14 (t, 1H); 3.88–3.85 (d, 1H); 3.04–2.89 (m, 2H); 2.64–2.59 (t, 1H); 2.23–2.18 (t, or q, 1H); 1.99–1.96 (d, 1H); 1.64–1.24 (d/q or t/t, 4H).

Mass Spec: Calculated: 441.37; Found: 441.1 [M+H]$^+$.

Example 14

2-bromo-4,5,6,7,9,9a,10,11,12,12a-decahydrocyclopenta[c][1,4]diazepino[6,7,1-ij]quinoline hydrochloride The compound from Example 13 (228 mg, 0.517 mmol) was dissolved in methylene chloride (0.800 mL). Trifluoromethane sulfonic acid (0.320 mL, 3.62 mmol) was added to the solution of Example 13 at room temperature, followed by anisole (0.168 mL, 1.55 mmol). After 1 hour, the reaction mixture was cooled to 0° C. After one hour, 1 N NaOH was added in an amount to turn the pH of the reaction mixture basic (the mixture turned yellow). Methylene chloride was added to dissolve the precipitate, and the mixture was transferred to separatory funnel. The reaction mixture was extracted with methylene chloride (3×), then the combined extracts were dried with magnesium sulfate, filtered and concentrated to give a brown oily solid (230 mg, >100% yield). Further purification (1% ammonia (2M solution in MeOH)/ethyl acetate, then 3% ammonia (2M solution in MeOH)/ethyl acetate, then 5% ammonia (2M solution in MeOH)/ethyl acetate) yielded 0.130 g of the free amine product (82%). The free amine product was dissolved (0.423 mmol) in diethyl ether and isopropyl alcohol. to the solution was then added HCl (2M solution in diethyl ether) (0.423 mmol). The solution was stirred for 30 min, and a dark yellow solid was filtered off.

$^1$H NMR (DMSO-d$_6$, 400 MHz): δ 7.36 (2H, s); 4.19–4.15 (1H, 2 d); 4.02–3.96 (1H, t and d); 3.78–3.68, (4H, bs); 3.38–3.34 (1H, 2 d); 3.15–2.99 (4H, m); 2.92–2.88 (1H, q); 2.62–2.55(t, 1H); 2.23–2.14 (2H, m); 1.96–1.92 (1H, m); 1.61–1.57(2H, m); 1.51–1.2(4H, m).

Mass Spec: Calculated: 307.23; Found: 309.01 [M+H]$^+$

Example 15

Benzyl 2-bromo-6,7,9,9a,10,11,12,13,14,14a-decahydrocyclohepta[c][1,4]diazepino[6,7,1-ij]quinoline-5(4H)-carboxylate Intermediate 3 (1 g, 2.77 mmol) was dissolved in methylene chloride (15 mL), and dimethoxymethane (0.735 mL, 8.30 mmol) and cycloheptene (0.646 mL, 5.54 mmol) were added at room temperature. The reaction flask was then cooled to 0° C., and then boron trifluoride diethyl etherate (0.386 mL, 3.05 mmol) was added slowly over 5 minutes. After 42 hours, another portion of dimethoxymethane (4.15 mmol, 1.5 eq), cycloheptene (2.77 mmol, 1 eq) and boron trifluoride diethyl etherate (1.52 mmol, 0.55 eq) were added. After a total of 48 hours, 1N NaOH was added to the reaction mixture in an amount to adjust the pH of the reaction mixture to about 9 to 10. Te contents of the flask were then transferred to a separatory funnel and extracted with methylene chloride (3×). The combined organic layers were then washed with brine (1×), dried with magnesium sulfate, filtered and concentrated to give a green substance. Further purification (10% ethyl acetate/hexane) yielded 0.806 g of desired product (62%).

$^1$H NMR (CDCl$_3$, 400 MHz): δ 7.37–7.29 (m, 5H); 7.17 (s, 1H); 7.03 (s, 1H); 5.06 (m, 2H); 4.56 & 4.45 (2d, 1H); 4.20 (d, 1H); 3.89 (2d, 1H); 3.39–3.27 (m, 1H); 3.03 (m, 2H); 2.87 (d, 1H); 2.78 (t, 1H); 2.06 (m, 2H); 1.89 (m, 3H); 1.73 (d, 2H); 1.59–1.35 (m, 3H); 1.18 (d, 1H); 1.00 (q, 1H).

Example 16

2-bromo-4,5,6,7,9,9a,10,11,12,13,14,14a-dodecahydrocyclohepta[c][1,4]diazepino[6,7,1-ij]quinoline hydrochloride The compound from Example 15 (1 g, 2.13 mmol) was dissolved in methylene chloride (2.3 mL) and cooled to 0° C. Trifluoromethane sulfonic acid (1.32 mL, 14.9 mmol) was added slowly to the solution followed by anisole (0.695 mL, 6.39 mmol). The reaction mixture was then stirred at 0° C. for 10 minutes, and then stirred at room temperature for 1 hour, at which point the reaction was complete. The pH of the reaction mixture was then adjusted with 1N NaOH until the pH was basic. The reaction mixture was then transferred to a separatory funnel and extracted with methylene chloride (3×). The combined organic extracts were dried with magnesium sulfate, filtered and concentrated to give a yellow oil. Further purification (2–4% ammonia in 2M solution in methanol/Ethyl acetate) yielded 0.630 g of the desired free amine product (88%). The free amine product (1.85 mmol) was then dissolved in diethyl ether and isopropanol. HCl in 2M solution of diethyl ether (1.85 mmol) was added. The solution was stirred for 30 minutes and a yellow solid was filtered off.

$^1$H NMR (DMSO-d$_6$, 400 MHz): δ 9.58 (bs, 1H); 9.38 (bs, 1H); 7.26 (d, 2H); 4.10–4.07 (d, 1H); 4.01–3.98 (d, 1H); 3.2–3.08 (m, 3H); 2.96–2.92 (d, 1H); 2.84–2.75 (d/t, 1H); 2.06–1.97 (t, 1H); 1.91–1.77 (m, 3H); 1.71–1.46 (m, 4H); 1.43–1.32 (q, 1H); 1.18–0.94 (m, 2H).

Mass Spec: Calculated: 335.29; Found: 335.1 [M+H]$^+$

Intermediate 4

7-chloro-2,3,4,5-tetrahydro-1H-1,4-benzodiazepine 7-chloro-3,4-dihydro-1H-1,4-benzodiazepine-2,5-dione (15.05 g, 71.4 mmol) was stirred in THF (120 mL). Lithium aluminum hydride (1M solution in THF, 214.5 mL, 214.4 mmol) was added gradually. When the addition was completed, the reaction mixture was heated to 63° C. and held for 19 hours. After 19 hours, the reaction was cooled to room temperature, and then to 0° C. The reaction mixture was quenched with water, 15% NaOH and another portion of water. After letting the reaction mixture stir for one hour, the precipitate was filtered off and washed with ethyl acetate. THF was removed, and the contents of the reaction flask were transferred to a separatory funnel with ethyl acetate and water. The contents in the separatory funnel were then extracted with ethyl acetate (3×). The combined organic extracts were washed with brine (2×), then dried with magnesium sulfate, filtered and concentrated to give the crude desired product. Further purification by recrystallization (methylene chloride) yielded orange crystals.

$^1$H NMR (CDCl$_3$, 400MHz): δ 7.05 (s, 1H); 6.99 (dd, J=8 Hz, 1H); 6.66 (d, J=4 Hz, 4Hz, 1H); 3.89 (bs, 1H); 3.82 (s, 2H); 3.03 (dt, 4H).

Intermediate 5

Benzyl 7-chloro-1,2,3,5-tetrahydro-4H-1,4-benzodiazepine-4-carboxylate

Intermediate 4 (5 g, 27.4 mmol) was dissolved in THF and cooled to 0° C. Hunig's Base (41.1 mmol) was then added, and over ten minutes benzyl chloroformate was added dropwise (30.1 mmol). After a 24 hour reaction hold period, the THF was removed, and water and ether were added to the flask. The reaction mixture was transferred to separatory funnel and extracted with ether (3×). The combined organic layers were washed with aqueous sodium bicarbonate (1×) and brine (1×), and then dried with magnesium sulfate, filtered and concentrated to give a yellow solid. Further purification (1–5% Ethyl acetate/methylene chloride) resulted in 7.7 g of desired product (88%).

$^1$H NMR (CDCl$_3$, 400 MHz): δ 7.36–7.28 (m, 5H); 7.06 (d, J=20, 1H); 7.02 (d, 1H); 6.67 (t, J=8,8, 1H); 5.07 (s, 2H); 4.36 (d, J=20, 2H); 3.67 (t, J=4, 8, 2H); 3.12 (t, 2H).

Mass Spec: Calculated: 316.79; Found: 317.03 [M+H]$^+$

Example 17

Benzyl 2-chloro-6,7,9,9a,10,11,12,12a-octahydrocyclopenta[c][1,4]diazepino[6,7,1-ij]quinoline-5(4H)-carboxylate Intermediate 5 (1 g, 3.15 mmol) was dissolved in methylene chloride (16 mL). Dimethoxymethane (0.840 mL, 9.47 mmol) and cyclopentene (0.555 mL, 6.31 mmol) were added and the reaction mixture was cooled to 0° C. Boron trifluoride diethyl etherate (0.440 mL, 3.47 mmol) was added slowly, and the reaction mixture was warmed to room temperature gradually and held for 28 hours. After 28 hours, another portion of dimethoxymethane, cyclopentene and boron trifluoride diethyl etherate (2 eq, 1.3 eq and 0.73 eq respectively) were added. After 18 hours, the pH of the reaction mixture was adjusted with 1N NaOH to a pH of 9 to 10, and stirred for 20 minutes. The reaction mixture was then transferred to a separatory funnel and extracted with methylene chloride (3×). The combined organic layers were washed with brine (1×), dried with magnesium sulfate, filtered and concentrated to give 1.46 g of a brown oil, the crude desired product. Further purification (10% ethyl acetate/hexane, then 15% ethyl acetate/hexane) afforded 0.807 g of the desired material with some baseline impurities. After a second purification (Methylene chloride+1% TEA) 0.750 g of the desired product was obtained (60%).

$^1$H NMR (DMSO-d$_6$, 400 MHz): δ 7.35 (m, 5H); 7.15–7.03 (2d, s, 2H); 5.02 (m, 2H); 4.57 (t, 1H); 4.17 (q, 1H); 3.86 (d, 1H); 3.31 (m, 4H); 2.95 (m, 3H); 2.63 (t, 1H); 2.21 (t, 1H); 1.98 (t, 1H); 1.64–1.24 (m, 3H)

Mass Spec: Calculated: 396.91; Found: 397.1 [M+H]$^+$.

Example 18

2-chloro-4,5,6,7,9,9a,10,10,11,12,12a-decahydrocyclopenta[c][1,4]diazepino[6,7,1-ij]quinoline hydrochloride The compound of Example 17 (0.527 g, 1.33 mmol) was dissolved in methylene chloride (2.5 mL). To this solution was added trifluoromethane sulfonic acid (0.822 mL, 9.29 mmol) and anisole (0.433 mL, 3.98 mmol). The reaction mixture was held at room temperature for 1 hour and then cooled to 0° C. The pH of the reaction mixture was then adjusted with 1 N NaOH until the pH was basic and then was stirred for 20 minutes. Methylene chloride was added and the reaction mixture was transferred to a separatory funnel. The reaction mixture was extracted with methylene chloride (3×), and the combined organic extracts were dried with magnesium sulfate, filtered and concentrated to give a brown oil (0.438 g). Subsequent purification (100% ethyl acetate, then changed to 5% ammonia in 2M solution of methanol/Ethyl acetate, then 10% ammonia in 2M solution of methanol/ethyl acetate) yielded 0.329 g of the free amine product (68%). The free amine (0.310 g, 1.18 mmol) was then dissolved in diethyl ether and isopropanol. To this solution was added HCl in 2M solution of diethyl ether (0.590 mL, 1.18 mmol). The solution was stirred for 30 minutes and then a yellow solid was filtered off and dried to give 0.300 g of final product.

$^1$H NMR (DMSO-d$_6$, 400 MHz): δ 7.24 (s, 2H); 4.18 (d, 1H); 4.00 (d, 1H); 3.36 (m, 1H); 3.18–3.00 (m, 5H); 2.9 (q, 1H); 2.59 (t, 1H); 2.17 (q, 2H); 1.93 (m, 1H); 1.61–1.48 (m, 2H); 1.32–1.19 (m, 2H)

Mass Spec: Calculated: 262.78; Found: 263.08 [M+H]$^+$

Example 19

Benzyl 2-chloro-6,7,9,9a,10,11,12,13,14,14a-decahydrocyclohepta[c][1,4]diazepino[6,7,1-ij]quinoline-5(4H)-carboxylate Intermediate 5 (1 g, 3.15 mmol) was dissolved in methylene chloride (16 mL). Dimethoxymethane (0.840 mL, 9.47 mmol) and cycloheptene (0.740 mL, 6.31 mmol), were added to the solution and the reaction mixture was cooled to 0° C. Boron trifluoride diethyl etherate was added slowly and the reaction mixture was warmed to room temperature gradually and held for 30 hours. At 30 hours, more boron trifluoride diethyl etherate, dimethoxymethane and cycloheptene were added (0.292 mL, 0.560 mL and 0.480 mL respectively). After 48 h, the pH was adjusted to a basic pH with N NaOH and stirred for 20 minutes. The contents of the reaction flask were transferred to a separatory funnel and extracted with methylene chloride (3×). The combined extracts were then washed with brine (1×), dried with magnesium sulfate, filtered and concentrated to give a brown oil. Further purification (10% ethyl acetate/hexane) resulted in 0.998 g of desired product (75%).

$^1$H NMR (CDCl$_3$, 400 MHz): δ 7.33 (m, 5H); 7.10–6.89 (3s, 2H); 5.05 (q, 2H); 4.58–4.55 (2d, 1H); 4.20 (d, 1H); 3.89 (2 d, 1H); 3.46 (b app d, 1H); 3.01 (t, 2H); 3.89 (d, 1H); 2.82 (t, 1H); 2.07 (q, 1H); 1.91 (q, 3H); 1.72 (d, 2H); 1.60–1.46 (m, 4H); 1.25–1.14 (m, 1H); 1.03 (q, 1H)

Mass Spec: Calculated: 424.97; Found: 425.08 [M+H]$^+$.

Example 20

2-chloro-4,5,6,7,9,9a,10,11,12,13,14,14a-dodecahydrocyclohepta[c][1,4]diazepino[6,7,1-ij]guinoline hydrochloride The compound of Example 19 (0.585 mg, 1.38 mmol) was dissolved in methylene chloride (2 mL) and cooled to 0° C. Trifluoromethane sulfonic acid (0.853 mL, 9.63 mmol) and anisole (0.449 mL, 4.13 mmol) were then added. The reaction mixture was stirred at 0° C. for 5 minutes and then held at room temperature for 1 hour. The reaction mixture was again cooled to 0° C. and the pH was adjusted until basic with 1N NaOH. The reaction mixture was transferred to a separatory funnel with methylene chloride and water, and extracted with methylene chloride (4×). The combined organic layers were then dried with magnesium sulfate, filtered and concentrated to give a yellow oil (0.584 g crude). Further purification (5% ammonia in 2M solution of methanol/ethyl acetate) yielded 0.336 g of the free amine product (84%). The free amine (0.392 g, 1.35 mmol) was dissolved in diethyl ether and HCl in 2M solution of diethyl ether (0.740 mL, 1.48 mmol) was added. After stirring for 30 minutes, the solid was filtered and air dried.

$^1$H NMR (DMSO-$d_6$, 400 MHz): δ 7.2 (d, 2H); 4.03 (2d, 2H); 3.57 (bs, 2H); 3.27 (q, 1H); 3.1 (hidden under water, ~2H); 2.96 (d, 1H); 2.88 (t, 2H); 2.01(bs, 1H); 1.91–1.71 (bd, 3H); 1.63–1.46 (m, 4H); 1.36 (q, 1H); 1.2 (s,1H); 1.01 (q, 1H);

Mass Spec: Calculated: 290.83; Found: 291.10 [M+H]$^+$

Intermediate 6

Benzyl 7-phenyl-1,2,3,5-tetrahydro-4H-1,4-benzodiazepine-4-carboxylate

Intermediate 3 (1 g, 2.77 mmol), phenyl boronic acid (0.506 g, 4.15 mmol), and 1,4 dioxane (16.3 mL) were heated to 80° C. Pd[p(o-tolyl)$_3$]$_2$Cl$_2$ (0.0653 g, 0.08 mmol), potassium carbonate (0.956 g, 6.92 mmol) and water (3.26 mL) were added and the reaction mixture was stirred for 2 hours. After 2 hours, the reaction mixture was cooled to room temperature, and the contents of the flask were filtered through a bed of celite, then the celite was washed with ethyl acetate and water. The filtrate was transferred to a separatory funnel and extracted with ethyl acetate (2×). The combined organic layers were washed with brine (1×), dried with magnesium sulfate, filtered and concentrated. Further purification (8:2 methylene chloride/hexane, then 100% methylene chloride when desired product came out) yielded the desired product as 0.754 g of a yellow oil (76%).

$^1$H NMR (CDCl$_3$, 400 MHz): δ 7.55(d, 1H); 7.40–7.23 (m, 11H); 6.82 (d, 1H); 5.07 (s, 2H); 4.48 (d, 2H); 40.73 (d, 2H); 3.20 (d, 2H)

Mass Spec: Calculated: 358.44; Found: 359.1 [M+H]$^+$

Example 21

Benzyl 2-phenyl-6,7,9,9a,10,11,12,12a-octahydrocyclopenta[c][1,4]diazepino[6,7,1-ij]quinoline-5(4H)-carboxylate Intermediate 6 (0.5 g, 1.34 mmol) was dissolved in methylene chloride (7 mL). To the solution of Interemdiate 6 was added dimethoxymethane (0.370 mL, 4.2 mmol) and cyclopentene (0.246 mL, 2.79 mmol) at room temperature. After cooling the reaction mixture to 0° C., boron trifluoride diethyl etherate (0.194 mL, 1.53 mmol) was added dropwise. The reaction mixture was then warmed to room temperature gradually and held for 24 hours. After 24 hours, the pH of the reaction mixture was adjusted to a pH of 10 with 1N NaOH. The contents of the flask were transferred to a separatory funnel and extracted with methylene chloride (3×). The combined extracts were then washed with brine (1×), dried with magnesium sulfate, filtered and concentrated. Further purification (1:1 hexane/methylene chloride, then 9:1 Hexane/ethyl acetate) yielded 0.343 g of a golden hard oil (56%).

$^1$H NMR (DMSO-$d_6$, 400 MHz): δ 7.59–7.53 (d, 1H); 7.42 (m, 5H); 7.33 (m, 5H); 7.25–7.17 (d,s, 1H); 7.12–7.04 (d, 1H); 4.99 (m, 2H); 4.67 (d, 1H); 4.27 (d, 1H); 3.90 (t, 1H); 3.02 (m, 3H); 41.70 (t, 1H); 2,28 (m, 1H); 2.00 (m, 1H); 1.66 (m, 1H); 1.55 (m, 1H); 1.41 (t, 1H); 1.28 (m, 1H).

Mass Spec: Calculated: 438.57; Found: 439.2 [M+H]$^+$

Example 22

2-phenyl-4,5,6,7,9,9a,10,11,12,12a-decahydrocyclopenta[c][1,4]diazepino[6,7,1-ij]quinoline hydrochloride The compound of example 21 (0.255 g, 0.581 mmol) was dissolved in methylene chloride (0.89 mL). To the solution of Example 21 was added trifluoromethane sulfonic acid (0.360 mL, 11.3 mmol) and anisole (0.190 mL, 1.74 mmol) at room temperature. After 45 minutes, the pH of the reaction mixture was adjusted to a pH of 9 to 10 with 1N NaOH, and then methylene chloride and water were added to the reaction flask. The contents of the flask were then transferred to a separatory funnel and extracted with methylene chloride (4×). The combined organic extracts were then dried with magnesium sulfate, filtered and concentrated. Further purification (10% ammonia in 2M solution of ethanol/ethyl acetate) yielded 0.157 g of the free amine product with some baseline impurities (80%). To purify further, the free amine was dissolved in diethyl ether/isopropanol, and then HCl in 2M solution of diethyl ether (1 eq) was added. After 30 minutes, the resulting precipitate was filtered to give the desired product.

$^1$H NMR (DMSO-$d_6$, 400 MHz): δ 7.64–7.28 (3d, 2t, m, 7H); 4.31 (2d, 1H); 4.17 (m, 1H); 3.46 (app t, 1H); 3.22 (m, 3H); 3.10–3.04 (d, t, 2H); 2.74 (t, 1H); 2.30 (m, 2H); 2.02 (m, 1H); 1.68 (d, 1H); 1.59 (m, 1H); 1.41 (m, 1H); 1.30 (m, 1H)

Mass Spec: Calculated: 304.43; Found: 305.1 [M+H]$^+$

Intermediate 7

7-methoxy-2,3,4,5-tetrahydro-1H-1,4-benzodiazepine

To a solution of 7-methoxy-3,4-dihydro-1H-1,4-benzodiazepine-2,5-dione (3.1 g, 15 mmol) in THF (26 mL), was added lithium aluminum hydride (1M solution in THF, 68 mL, 68 mmol) by dropwise addition over 20 minutes. The reaction was heated to 74° C. and held for 24 hours. After 24 hours, the reaction was quenched with water, 15% NaOH and another portion of water. The reaction mixture was then diluted with ethyl acetate and sodium sulfate was added. The reaction mixture was then stirred for 1 hour, after which it was filtered through a bed of celite, with subsequent washing of the bed with ethyl acetate. The solvent was removed from the filtrate to give the crude desired product. Further purification (1% ammonia in 2M solution of ethanol/ethyl acetate, then 3%, then 5%) yielded 1.9 g of the desired product as orange crystals (71%).

$^1$H NMR (DMSO-d$_6$, 400 MHz): δ 6.77 (d, J=8 Hz, 1H); 6.65 (ds, 1H); 6.58 (dt, J=4 Hz, 4 Hz, 1H); 5.04 (bs, 1H); 3.65 (s, 3H); 3.62 (s, 2H); 2.81 (d, 4H).

Mass Spec: Calculated: 178.23; Found: 179.1 [M+H]$^+$

Intermediate 8

Benzyl 7-methoxy-1,2,3,5-tetrahydro-4H-1,4-benzo-diazepine-4-carboxylate

Intermediate 7 (1.5 g, 8.4 mmol) was dissolved in methylene chloride (42 mL) and cooled to 0° C. Hunig's base (2.20 mL, 12.6 mmol) and benzylchloroformate (1.32 mL, 9.26 mmol) were then added, and the reaction mixture was warmed to room temperature. After a 4 hour period, the contents of the flask were transferred to a separatory funnel and extracted with methylene chloride (3×). The combined organic extracts were washed with saturated sodium bicarbonate (1×) and brine (1×), and then dried with magnesium sulfate, filtered and concentrated. Further purification (8:2 Hexane/ethyl acetate, then 1:1 Hexane/ethyl acetate) yielded 1.25 g of desired product (50%).

$^1$H NMR (DMSO-d$_6$, 400 MHz): δ 7.33 (m, 5H); 6.80 (d, J=4 Hz, 1H); 6.71–6.64 (d, 1H); 5.27 (bs, 1H); 5.04 (s, 2H); 4.31 (d, J=8 Hz, 2H); 3.67 (s, 1H); 3.59 (s, 2H); 3.54 (s, 1H); 2.95 (s, 2H).

Mass Spec: Calculated: 312.37; Found: 313.1 [M+H]$^+$

Example 23

Benzyl 2-methoxy-6,7,9,9a,10,11,12,12a-octahydro-cyclopenta[c][1,4]diazepino6,7,1-ij]quinoline-5(4H)-carboxylate To a solution of Intermediate 8 (0.5 g, 1.67 mmol) in methylene chloride (8 mL) was added dimethoxymethane (0.330 mL, 3.35 mmol) and cyclopentene (0.40 mL, 5.0 mmol) at room temperature. After the reaction mixture was cooled to 0° C., boron trifluoride diethyl etherate (0.234 mL, 1.84 mmol) was added slowly. The reaction mixture was adjusted to room temperature gradually and held for 120 hours. After the 120 hours, the pH of the reaction mixture was adjusted to a pH of 12 with 1N NaOH, and then water and methylene chloride were added. The reaction mixture was then extracted with methylene chloride (3×). The combined organic layers were washed with brine (1×), dried with magnesium sulfate, filtered and concentrated. Further purification (9:1 Hexane/ethyl acetate, then 75:25 hexane/ethyl acetate, then 1:1 hexane/ethyl acetate) yielded 0.371 g of desired product (56%).

$^1$H NMR (DMSO-d$_6$, 400 MHz): δ 7.33 (m, 5H); 6.69 (s, 1H); 6.63–6.54 (s, 1H); 5.07–4.94 (m, 2H); 4.53 (m, 1H); 4.15 (major rotomer, d, 1H); 4.09 (minor rotomer, d,); 3.89 (t, 1H); 3.69 (s, 1H); 3.60 (s, 2H); 3.12 (d, 1H); 2.95 (dd, 1H) 2.88 (q, 1H); 2.83 (t, 1H); 2.61 (t, 1H); 2.22 (43, 2H); 1.99 (m, 1H); 1.64 (m, 1H); 1.53 (m, 1H); 1.33 (m, 1H); 1.22 (m, 1H).

Mass Spec: Calculated: 392.50; Found: 393.1 [M+H]$^+$

Example 24

2-methoxy-4,5,6,7,9,9a,10,11,12,12a-decahydrocy-clopenta[c][1,4]diazepino[6,7,1-ij]quinoline hydrochloride To a solution of the compound of Example 23 (0.315 g, 0.803 mmol) in methylene chloride (1.2 mL) were added trifluoromethane sulfonic acid (0.497 mL, 5.61 mmol) and anisole (0.262 mL, 2.41 mmol) at room temperature. After 90 minutes the reaction was complete. The reaction mixture was basified with 1N NaOH (pH=12), and diluted with water and methylene chloride. The contents of the flask were transferred to a separatory funnel, and extracted with methylene chloride (4×). Then the combined organic layers were dried with magnesium sulfate, filtered and concentrated to give the crude desired product. Further purification (10% ammonia in 2M solution of ethanol/ethyl acetate) yielded 0.150 g of a yellow solid (73%). The free amine was then dissolved in diethyl ether, and a 2M solution of hydrogen chloride in diethyl ether (1 eq) was added. After stirring for 30 minutes, the resulting precipitate was filtered to give a pale yellow solid.

$^1$H NMR (DMSO-d$_6$, 400 MHz): δ 9.72 (bs); 8.70 (bs); 6.87 (d, 1H); 6.83 (d, J=4 Hz, 1H); 4.17–4.15 (d, 1H); 4.07 (t, J=8 Hz, 8 Hz, 1H); 3.72 (s, 3H); 3.33 (d, 1H); 3.16 (m, 2H); 3.03 (m, 2H); 2.94 (q, 1H); 2.63 (t, 1H); 2.24 (m, 2H); 2.00 (m, 1H); 1.66 (m, 1H); 1.56 (m, 1H); 1.35 (m, 1H); 1.25 (m, 1H).

Mass Spec: Calculated: 258.36; Found: 259.1 [M+H]$^+$

Intermediate 9

8-fluoro-2,3,4,5-tetrahydro-1H-1,4-benzodiazepine

THF (19.1 mL) was added to a flask containing 8-fluoro-3,4-dihydro-1H-1,4-benzodiazepine-2,5-dione (2.11 g, 10.9 mmol). Dropwise over 10 minutes was added lithium aluminum hydride in 1M THF (48.9 mL, 48.9 mmol). The reaction mixture was heated to reflux for 5.5 hours, and then let cool to room temperature overnight. After 18 hours, no starting material was seen. The reaction was quenched with water, 15% sodium hydroxide and another portion of water. After the white precipitate was filtered off, THF was removed from the filtrate. The contents of the flask were then transferred to a separatory funnel using ethyl acetate and water, and extracted with ethyl acetate (3×). The combined organic extracts were washed with brine (1×) and then dried with magnesium sulfate, filtered and concentrated to give a yellow oil. Further purification (15% ammonia 2M solution in ethanol/ethyl acetate) yielded the desired compound.

$^1$H NMR (CDCl$_3$, 400 MHz): δ 7.02 (t, J=4, 8 Hz, 1H); 6.54–6.41 (m, 2H); 3.82 (s, 2H); 3.09 (t, 2H); 3.02 (t, 2H); 1.72 (bs, 1H)

Mass Spec: Calculated=166.1982; Found=167.1 [M+H]$^+$

Intermediate 10

Benzyl 8-fluoro-1,2,3,5-tetrahydro-4H-1,4-benzodi-azepine-4-carboxylate

Intermediate 9 (0.450 g, 2.7 mmol) was dissolved in methylene chloride (13.5 mL) and then cooled to 0° C. Hunig's Base (0.707 mL, 4.06 mmol) and benzyl chloroformate (0.386 mL, 2.7 mmol) were added and the reaction mixture was warmed to room temperature. After 3.5 days at room temperature, the contents of the flask were transferred to a separatory funnel, and washed with water (1×) and extracted with methylene chloride (3×). The combined organic layers were washed with saturated sodium bicarbonate and brine (1× each) and dried with magnesium sulfate, filtered and concentrated to give the crude product as a yellow oil. Further purification (20% ethyl acetate/hexane+1% TEA) yielded 0.460 g of the desired product as a green oil (56%).

¹H NMR (CDCl₃, 400 MHz): δ 7.35–7.24 (m, 5H); 6.99 (t, 1H); 6.50 (d, 2H); 5.07 (s, 2H); 4.40 (d, 2H); 3.70 (d, 2H); 3.17 (d, 2H).
Mass Spec: Calculated: 300.33; Found: 301.1 [M+H]⁺

Example 25

Benzyl 1-fluoro-6,7,9,9a,10,11,12,12a-octahydrocyclopenta[c][1,4]diazepino[6,7,1-ij]quinoline-5(4H)-carboxylate To a solution of Intermediate 10 (0.75 g, 2.5 mmol) and methylene chloride (12.5 mL) were added dimethoxymethane (0.663 mL, 74.9 mmol) and cyclopentene (0.439 mL, 49.9 mmol). The reaction mixture was cooled to 0° C. and boron trifluoride diethyl etherate (0.348 mL, 2.75 mmol) was added dropwise. The reaction mixture was warmed to room temperature. After a 24 hour period, additional boron trifluoride (0.73 eq), dimethoxymethane (2 eq) and cyclopentene (1.3 eq) were added. After 48 hours, the pH of the reaction mixture was adjusted to a pH of 8 to 9 with 1N sodium hydroxide. The contents of the flask were then transferred to a separatory funnel and extracted with methylene chloride (3×). The combined extracts were washed with brine (1×), dried with magnesium sulfate, filtered and concentrated to give a yellow oil. Further purification (5% TEA/hexane) yielded 0.664 g of desired product (70%).
¹H NMR (DMSO-d₆, 400 MHz): δ 7.39–7.26 (m, 5H); 6.97 (dt, 1H); 6.60 (t, 1H); 5.03 (q, 2H); 4.60 (m, 1H); 3.86 (d, 1H); 3.32 (d, 1H under water peak); 3.00 (d, 2H); 2.94 (q, 2H); 2.69 (t, 1H); 2.23 (m, 1H); 2.18 (m, 1H); 1.96 (, 1H); 1.64 (m, 1H); 1.57 (m, 1H); 1.28 (t, 2H).
Mass Spec: Calculated: 380.4622; Found: 381.1 [M+H]⁺

Example 26

1-fluoro-4,5,6,7,9,9a,10,11,12,12a-decahydrocyclopenta[c][1,4]diazepino[6,7,1-ij]quinoline hydrochloride The compound of Example 25 (0.350 g, 0.92 mmol) was dissolved in methylene chloride (1.41 mL). Trifluoromethane sulfonic acid (0.570 mL, 6.4 mmol) and anisole (0.300 mL, 2.7 mmol) were added at room temperature. After 4.5 hours, the pH of the reaction mixture was adjusted to a pH of 8 to 9 with 1N NaOH, and the solution was stirred for 20 minutes. The contents of the flask were transferred to a separatory funnel and extracted with methylene chloride (3×). The combined organic extracts were dried with magnesium sulfate, filtered and concentrated. Further purification (15% ammonia in 2M solution ethanol/ethyl acetate) gave 0.1514 g of the desired free amine product as a yellow oil (67%). The free amine product (0.1514 g, 0.61 mmol) was dissolved in diethyl ether, and then HCl in 2M solution of diethyl ether was added. The mixture was stirred for 30 minutes and a pale yellow solid was filtered off.
¹H NMR (CDCl₃, 400 MHz): δ 10.09 (bs); 9.21 (bs); 7.12 (t, 1H); 6.62 (t, 1H); 4.26(d, 1H); 4.14(t, 1H); 3.42(s, 3H); 3.27(d, 1H); 3.03–2.91(m, 2H); 2.8 (t, 1H); 2.35(m, 1H); 2.15(d, 1H); 2.01(m, 1H); 1.75–1.56 (m, 2H); 1.28 (t, 2H)
Mass Spec: Calculated: 246.33; Found: 247.1 [M+H]⁺

Example 27

Benzyl 1-fluoro-6,7,9,9a,10,11,12,13,14,14a-decahydrocyclohepta[c][1.4]diazepino[6,7,1-ij]quinoline-5(4H)-carboxylate To a solution containing Intermediate 10 (0.75 g, 2.5 mmol) in methylene chloride (12.5 mL) were added dimethoxymethane (0.663 mL, 74.9 mmol) and cycloheptene (0.583 mL, 49.9 mmol). The reaction mixture was cooled to 0° C. and boron trifluoride diethyl etherate (0.348 mL, 2.75 mmol) was added dropwise. The reaction mixture was warmed to room temperature and after 24 hours, an additional amount of boron trifluoride (0.73 eq), dimethoxymethane (2 eq) and cyclopentene (1.3 eq) was added. After 48 hours, 1N sodium hydroxide was added in an amount to bring the pH of the reaction mixture to 8 to 9. The contents of the flask were transferred to a separatory funnel and extracted with methylene chloride (3×). The combined extracts were washed with brine (1×), dried with magnesium sulfate, filtered and concentrated to give a yellow oil. Further purification (5% TEA/hexane) yielded 0.620 g of desired product (61%).
¹H NMR (DMSO-d₆, 400 MHz): δ 7.39–7.22 (m, 5H); 6.95 (dt, J=8,16, 1H); 6.55 (t, J=4,6, 1H); 5.03 (q, 2H); 4.52 (2 d, 1H); 4.26 (t, 1H); 3.85(bm, 1H); 3.42 (t, 2H under water peak); 3.02 (q, 1H); 2.94 (d, 2H); 2.85 (t, 1H); 1.97 (t, 2H); 1.85 (d, 2H); 1.70 (t, 1H); 1.54–1.4 (m, 4H); 1.17 (t, 1H); 0.97 (q, 1H).
Mass Spec: Calculated: 408.51; Found: 409.2 [M+H]⁺

Example 28

1-fluoro-4,5,6,7,9,9a,10,11,12,13,14,14a-dodecahydrocyclohepta[c][1,4]diazepino[6,7,1-ij]quinoline hydrochloride To a solution containing the compound of Example 27 (0.310 g, 0.75 mmol) in methylene chloride (1.15 mL) were added trifluoromethane sulfonic acid (0.470 mL, 5.3 mmol) and anisole (0.247 mL, 2.27 mmol) at room temperature. After 4.5 hours, 1N NaOH was added in an amount sufficient to bring the pH of the reaction mixture to basic. The contents of the flask were transferred to a separatory funnel and extracted with methylene chloride (3×). The combined organic extracts were dried with magnesium sulfate, filtered and concentrated to give crude product. Further purification (15% ammonia in 2M solution of ethanol/ethyl acetate) gave 0.1335 g of free amine product (64%). The free amine (0.1335 g, 0.49 mmol) was dissolved in diethyl ether, and then HCl in 2M solution of diethyl ether (0.245 mL, 0.49 mmol) was added. This mixture was stirred for 30 minutes and the yellow solid was filtered.
¹H NMR (DMSO-d₆, 400 MHz): δ 9.22 (bs); 7.18 (t, 1H); 6.67 (t, 1H); 4.10 (d, 1H); 4.01 (d, 1H); 3.34(m, 2H); 3.14 (m, 3H); 2.95 (d, 2H); 2.80 (t, 1H); 1.93(m, 2H); 1.82(t, 1H); 1.78 (m, 2H); 1.43(m, 4H); 1.16(m, 1H); 0.95(q, 1H)
Mass Spec: Calculated: 274.38; Found: 275.1 [M+H]⁺.

Intermediate 11

8-(trifluoromethyl)-2,3,4,5-tetrahydro-1H-1,4-benzodiazepine

To a solution of 8-(trifluoromethyl)-3,4-dihydro-1H-1,4-benzodiazepine-2,5-dione (1.5 g, 6.1 mmol) in THF (11 mL) at room temperature was added lithium aluminum hydride in THF (28 mL, 28 mmol) over 10 minutes. Once the addition was completed, the reaction was heated to 68° C. After 24 hours, additional lithium aluminum hydride in THF was added (12.3 mmol) over five minutes. After 3 hours, the reaction mixture was cooled to 0° C., and then quenched with water, 15% NaOH, and an additional portion of water. After filtering off the gray precipitate and rinsing with ethyl acetate, the solvent was removed from the filtrate. The resulting solid was then redissolved in ethyl acetate and transferred to a separatory funnel and washed with water (3×), dried with magnesium sulfate, filtered and concentrated to give a yellow solid. Further purification (15% ammonia in 2M solution of ethanol/ethyl acetate) yielded 0.918 g of desired product (69%).

$^1$H NMR (CDCl$_3$, 400 MHz): δ 7.16 (d, J=8 Hz, 1H); 7.03 (d, J=8 Hz, 1H); 6.97 (s, 1H); 4.04 (bs, 1H); 3.90 (s, 2H); 3.10 (d, J=4 Hz, 2H); 3.04 (m, J=4 Hz, 8 Hz, 2H); 1.56 (bs, 1H)

Mass Spec: Calculated: 216.20; Found: 217.0 [M+H]$^+$

Intermediate 12

Benzyl 8-(trifluoromethyl)-1,2,3,5-tetrahydro-4H-1,4-benzodiazepine-4-carboxylate Intermediate 11 (0.818 g, 3.78 mmol) was dissolved in methylene chloride (19 mL) and then cooled to 0° C. Hunig's Base (0.989 mL, 5.68 mmol) and benzyl chloroformate (0.594 mL, 4.16 mmol) were then added and the reaction mixture was warmed to room temperature. After 90 minutes, the reaction was completed. The contents of the flask were transferred to a separatory funnel, and water was added. The aqueous layer was extracted with methylene chloride (3×), and the combined organic layers were washed with saturated sodium bicarbonate (1×) and brine (1×). The organic layer was then dried with magnesium sulfate, filtered and concentrated to give a brown oil. Further purification (Methylene chloride) yielded 0.697 g of desired product (53%).

$^1$H NMR (CDCl$_3$, 400 MHz): δ 7.35 (m, 5H); 7.23, 7.13, 6.98 (d, d, s, 3H total); 5.06 (s, major rotomer), 5.04 (s, minor rotomer), total 2H; 4.45 (d, 2H); 3.70(sd, 2H); 3.20 (dt, 2H).

Mass Spec: Calculated: 350.34; Found: 351.0 [M+H]$^+$

Example 29

Benzyl 1-(trifluoromethyl)-6,7,9,9a,10,11,12,12a-octahydrocyclopenta[c][1,4]diazepino[6,7,1-ij]quinoline-5(4H)-carboxylate To a solution containing Intermediate 12 (0.5 g, 1.4 mmol) dissolved in methylene chloride (7 mL) were added dimethoxymethane (0.38 mL, 4.3 mmol) and cyclopentene (0.251 mL, 2.85 mmol) at room temperature. the reaction mixture was then cooled to 0° C. and boron trifluoride diethyl etherate (0.199 mL, 1.57 mmol) was added dropwise. After 24 hours, the reaction was complete and was basified to a pH of 10 with 1N NaOH. The contents of the flask were transferred to a separatory funnel and extracted with methylene chloride (3×). The combined extracts were washed with brine (1×), dried with magnesium sulfate, filtered and concentrated to yield the crude product. Further purification (1:1 hexane/methylene chloride) yielded 0.366 g of the desired material (60%).

$^1$H NMR (DMSO-d$_6$, 400 MHz): δ 7.33–7.07 (tsdt, 8H); 5.04 (d split, 2H); 4.61 (2d, 1H); 4.52–4.44 (sds, 1H); 3.87 (b2 d, 1H); 3.55 (m, 1H); 3.36 (m, 1H); 3.18 (s, 2H); 3.01 (m, 1H); 2.83 (q, 1H); 2.22 (bt, 1H); 2.12 (m, 1H); 1.90 (m, 1H); 1.70 (m, 1H); 1.60 (m, 1H); 1.47 (m, 1H); 1.36 (m, 1H); 1.24 (s, 1H).

Mass Spec: Calculated: 430.47; Found: 431.1 [M+H]$^+$

Example 30

1-(trifluoromethyl)-4,5,6,7,9,9a,10,11,12,12a-decahydroyclopenta[c][1,4]diazepino[6,7,1-ij]quinoline hydrochloride To a solution containing the compound of example 29 (0.345 g, 0.80 mmol) dissolved in methylene chloride (1.2 mL) were added trifluoromethane sulfonic acid (0.496 mL, 5.6 mmol) and anisole (0.261 mL, 2.4 mmol) at room temperature. After 1 hour, the reaction was completed and the reaction mixture was basified to a pH of 12 with 1N NaOH. Water and methylene chloride were added and the reaction mixture was stirred for 45 minutes. The contents of the flask were transferred to a separatory funnel, and the aqueous layer was extracted with methylene chloride (4×). The combined organic layers were dried with magnesium sulfate, filtered and concentrated to give yellow oil. Further purification (10% ammonia in 2M solution of ethanol//Ethyl acetate) yielded 0.190 g of the free amine product (80%). The free amine was then taken and converted into the hydrochloride salt. After the compound was dissolved in diethyl ether, HCl in a 2M solution in diethyl ether (0.32 mL, 0.64 mmol) was added. After the mixture stirred for 30 minutes, the resulting yellow precipitate was filtered off to give 0.1932 g of the desired product.

$^1$H NMR (DMSO-d$_6$, 400 MHz): δ 7.38 (d, J=4 Hz, 1H); 7.23 (d, J=8 Hz, 1H); 4.24 (q, 2H); 3.52 (dt, 1H); 3.31–3.20 (m, 4H); 3.12 (2 d, 1H); 2.85 (t, 1H); 2.21 (m, 2H); 1.92 (m, 1H); 1.67 (m, 2H); 1.45 (m, 2H).

Mass Spec: Calculated: 296.33; Found: 297.1 [M+H]$^+$

Intermediate 13

8-fluoro-7-methoxy-2,3,4,5-tetrahydro-1H-1,4-benzodiazepine

To a solution of 8-fluoro-7-methoxy-3,4-dihydro-1H-1,4-benzodiazepine-2,5-dione (5.1 g, 227 mmol) dissolved in THF (39.8 mL) was added lithium aluminum hydride (1M solution in THF, 102.4 mL, 102.4 mmol) dropwise. The reaction mixture was heated to reflux. After 26 hours, an additional equivalent of lithium aluminum hydride in THF (22.7 mmol) was added. At 30 hours, the reaction was quenched with water, 15% NaOH and an additional portion of water. The precipitate was filtered and washed with ethyl acetate. THF was removed from the filtrate, and then ethyl acetate and water were added to the flask. All the contents in the flask were transferred to the separatory funnel and extracted with ethyl acetate (3×). The combined organic layers were then washed with brine (1×), dried with magnesium sulfate, filtered and concentrated to give a brown oil. Further purification (15% ammonia in 2M solution of ethanol/ethyl acetate) yielded the desired product.

$^1$H NMR (DMSO-d$_6$, 400 MHz): δ 6.82 (d, J=8 Hz, 1H); 6.65 (d, 1H, J=12 Hz,1H); 5.2 (bs, 1H); 3.68 (s, 3H); 3.58 (s, 2H); 2.80 (dt, J=4 Hz, 2H); 2.74 (dt, J=4 Hz, 2H)

Intermediate 14

Benzyl 8-fluoro-7-methoxy-2,3,4,5-tetrahydro-1H-1-benzazepine-4-carboxylate

Intermediate 13 (1.4 g, 7.13 mmol) was dissolved in methylene chloride (35.6 mL) and then cooled with an ice bath to 0° C. Hunig's Base (1.86 mL, 10.7 mmol) and benzylchloroformate (1.02 mL, 7.13 mmol) were added, and the reaction mixture was warmed to room temperature after the additions were complete. After 1 hour the reaction was complete. The contents of flask were transferred to a separatory funnel and washed with water (1×). The aqueous layer was extracted with methylene chloride (2×). The combined organic layers were washed with aqueous sodium bicarbonate (1×) and brine (1×), dried with magnesium sulfate, filtered and concentrated to give a yellow oil as the crude desired product. Further purification (65:35 Hexane/Ethyl acetate) yielded 1.8 g of a yellow solid (78%).

$^1$H NMR (DMSO-$d_6$, 400 mHz); δ 7.27 (m, 5H); 6.88–6.73 (2d, 1H); 6.66 (d, 1H); 5.42 (d, 1H); 4.99 (s, 2H); 4.28 (s, 2H); 3.70 (s, 1H); 3.53 (t, 4H); 2.96 (bs, 2H).

Mass Spec: Calculated: 330.36; Found: 331.1 [M+H]$^+$

Example 31

Benzyl 1-fluoro-2-methoxy-6,7,9,9a,10,11,12,12a-octahydrocyclopenta[c][1,4]diazepino[6,7,1-ij] quinoline-5(4H)-carboxylate To a solution containing Intermediate 14 (0.600 g, 1.81 mmol) dissolved in methylene chloride (9 mL) were added dimethoxymethane (0.482 mL, 5.45 mmol) and cyclopentene (0.319 mL, 3.63 mmol) at room temperature. The reaction mixture was cooled to 0° C., and boron trifluoride diethyl etherate (0.253 mL, 1.99 mmol) was added. At 24 hours, a second portion of dimethoxymethane (2 eq), cyclopentene (1.3 eq) and boron trifluoride diethyl etherate (0.73 eq) were added. At 48 hours, a third portion of dimethoxymethane (2.25 eq), cyclopentene (1.5 eq) and boron trifluoride diethyl etherate (0.825 eq) were added. After 72 hours, the reaction mixture was basified with 1N NaOH. The contents of the flask were transferred to a separatory funnel and extracted with methylene chloride (3×). The combined organic layers were washed with brine (1×), dried with magnesium sulfate, filtered and concentrated to give the desired product, 0.830 g.

$^1$H NMR (DMSO-$d_6$, 400 MHz); δ 7.29 (s, 5H); 6.85 & 6.67 (d, 1H); 5.71 (s, 1H); 4.97 (m, 2H); 4.50 (d, 1H); 4.09 (d, 1H); 3.85–3.72 (t,s, 1H); 3.19–3.09 (m, 2H); 2.91 (m, 2H); 2.59 (t, 1H); 2.21–2.12 (m, 2H); 1.89 (m, 1H); 1.61–1.47 (m, 2H); 1.20 (q, 2H)

Example 32

1-fluoro-2-methoxy-4,5,6,7,9,9a,10,11,12,12a-decahydrocyclopenta[c][1,4]diazepino[6,7,1-ij] quinoline hydrochloride To a solution containing the compound from example 31 (0.4 g, 0.98 mmol) dissolved in methylene chloride (1.5 mL) were added trifluoromethane sulfonic acid (0.603 mL, 6.82 mmol) and anisole (0.318 mL, 2.92 mmol) at room temperature. After 5 hours, more trifluoromethane sulfonic acid (3.5 eq) was added. After 8 hours, the reaction was basified with 1N NaOH. The contents of the flask were transferred to a separatory funnel and extracted with methylene chloride (3×). The combined organic extracts were dried with magnesium sulfate, filtered and concentrated to give crude product. Further purification (5% ammonia in 2M solution of ethanol/ethyl acetate) gave 0.191 g of free amine product with some small impurities (71% yield). The free amine product (0.191 g) was dissolved in ethyl acetate and a white solid was precipitated out. After drying, 0.142 g of the free amine product was obtained (53%). The free amine (0.142 g, 0.514 mmol) was dissolved in diethyl ether and HCl in 2M solution of diethyl ether (0.257 mL, 0.514 mmol) was added. The mixture was stirred for 30 minutes, then the solid was filtered off.

$^1$H NMR (DMSO-$d_6$, 400 MHz): δ 7.18 (d, 1H); 4.22 (d, 1H); 4.03 (d, 1H); 3.79 (s, 3H); 3.19 (d, 1H); 3.15–3.07 (m, 1H); 3.01 (m, 3H); 2.66 (t, 1H); 2.25 (m, 2H); 2.21–1.95 (m, 1H); 1.69–1.58 (m, 3H); 1.28 (m, 2H).

Mass Spec: Calculated: 276.35; Found: 277.1 [M+H]$^+$.

Example 33

Benzyl 1-fluoro-2-methoxy-6,7,9,9a,10,11,12,13,14, 14a-decahydrocyclohepta[c][1,4]diazepino[6,7,1-ij] quinoline-5(4H)-carboxylate To a solution containing Intermediate 14 (0.600 g, 1.81 mmol) dissolved in methylene chloride (9 mL), was added dimethoxymethane (0.482 mL, 5.45 mmol) and cycloheptene (0.424 mL, 3.63 mmol) at room temperature. The reaction was cooled to 0° C., and boron trifluoride diethyl etherate (0.253 mL, 1.99 mmol) was added. At 24 hours, a second portion of dimethoxymethane (2 eq), cyclopentene (1.3 eq) and boron trifluoride diethyl etherate (0.73 eq) was added. After 48 hours, the reaction was basified with 1N NaOH. The contents of the flask were transferred to a separatory funnel and extracted with methylene chloride (3×). The combined organic layers were washed with brine (1×), dried with magnesium sulfate, filtered and concentrated to give the desired product, 0.861 g.

$^1$H NMR (DMSO-$d_6$, 400 MHz): δ 7.38 (s, 4H); 6.80 (d, 1H); 6.67 (d, 1H); 5.71 (t, 1H); 4.99 (q, 2H); 4.46 (d, 1H); 4.12 (d, 1H); 3.78 & 3,71 (d,s, 2H); 3.53 (s, 2H); 3.20–3.09 (m, 1H); 2.82 (m, 3H); 2.03 (m, 1H); 1.89 (m, 1H); 1.80 (d, 2H); 1.64 (t, 2H); 1.43 (m, 4H); 1.12 (d, 1H); 0.90 (q, 1H).

Example 34

1-fluoro-2-methoxy-4,5,6,7,9,9a,10,11,12,13,14,14a-dodecahydrocyclohepta[c][1,4]diazepino[6,7,1-ij] quinoline hydrochloride To a solution containing the compound from example 33 (0.4 g, 0.9 mmol) dissolved in methylene chloride (1.35) were added trifluoromethane sulfonic acid (0.545 mL, 6.16 mmol) and anisole (0.287 mL, 2.64 mmol) at room temperature. After 5 hours, more trifluoromethane sulfonic acid (3.5 eq) was added. After 8 hours, the reaction was basified with 1N NaOH. The contents of the flask were transferred to a separatory funnel and extracted with methylene chloride (3×). The combined organic extracts were dried with magnesium sulfate, filtered and concentrated to give the crude product. Further purification (15% ammonia in 2M solution of ethanol/ethyl acetate) gave 0.172 g of desired free amine product (65%). The free amine (0.172 g, 0.565 mmol) was dissolved in diethyl ether and HCl in 2M solution of diethyl ether (0.282 mL, 0.565 mmol) was added. The mixture was stirred for 30 minutes after which the solid was filtered off and air dried.

$^1$H NMR (DMSO-$d_6$, 400 MHz): δ 9.75 (bs); 8.88 (bs); 7.17 (d, 1H); 4.15(2d, 1H); 4.03 (t, 1H); 3.32(d, 1H); 3.15 (q, 2H); 3.05–2.91 (m, 3H); 2.81 (t, 1H); 2.02–1.93 (m, 2H); 1.86 (s, 2H); 1.73 (bs, 1H); 1.52–1.42 (m, 4H); 1.24–1.13 (m, 1H); 0.95 (q, 1H)

Mass Spec: Calculated: 304.41; Found: 305.2 [M+H]$^+$

What is claimed is:

1. A compound of Formula I or a pharmaceutically acceptable salt thereof:

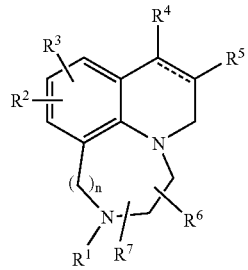

I wherein $R^1$ is hydrogen, alkyl of 1 to 6 carbon atoms, alkanoyl of 2 to 6 carbon atoms, or carboarylalkoxy of 7 to 11 carbon atoms;

$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;

$R^4$ and $R^5$ are taken together with the carbons to which they are attached, to form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;

$R^6$ and $R^7$ are each, independently, hydrogen or alkyl of 1 to 6 carbon atoms;

n is 1; and a dotted line represents an optional double bond.

2. The compound of claim 1 wherein, $R^2$ and $R^3$ independently, are hydrogen, halogen, cyano, perfluoralkyl of 1 to 3 carbon atoms, phenyl or alkoxy of 1 to 3 carbon atoms.

3. The compound of claim 1 wherein $R^4$ and $R^5$ are taken together, along with the carbon atoms to which they are attached, to form a cycloalkane or cycloalkene moiety of 5 to 8 carbon atoms, where one or more of the carbon atoms are optionally substituted by alkyl of 1 to 4 carbon atoms.

4. The compound of claim 1 wherein $R^4$ and $R^5$ are taken together, along with the carbon atoms to which they are attached, to form a cycloalkane moiety of 5 to 7 carbon atoms.

5. The compound of claim 1 wherein $R^1$, $R^6$ and $R^7$ are hydrogen.

6. The compound of claim 1 wherein $R^2$ and $R^3$ are independently selected from hydrogen, halogen, trifluoromethyl, phenyl or alkoxy of 1 to 3 carbon atoms; $R^1$, $R^6$ and $R^7$ are each hydrogen; and $R^4$ and $R^5$ taken together with the carbon atoms to which they are attached, form cyclopentane, cyclohexane or cycloheptane.

7. The compound of claim 1 selected from:
4,5,6,7,9,9a,10,11,12,12a-decahydrocyclopenta[c][1,4]diazepino[6,7,1-ij] quinoline;
2-bromo-4,5,6,7,9,9a,10,11,12,12a-decahydrocyclopenta[c][1,4]diazepino [6,7,1-ij]quinoline;
2-chloro-4,5,6,7,9,9a,10,11,12,12a-decahydrocyclopenta[c][1,4]diazepino [6,7,1-ij]quinoline;
2-phenyl-4,5,6,7,9,9a,10,11,12,12a-decahydrocyclopenta[c][1,4]diazepino [6,7,1-ij]quinoline;
2-methoxy-4,5,6,7,9,9a,10,11,12,12a-decahydrocyclopenta[c][1,4]diazepino [6,7,1-ij]quinoline;
1-fluoro-4,5,6,7,9,9a,10,11,12,12a-decahydrocyclopenta[c][1,4]diazepino [6,7,1-ij]quinoline;
1-(trifluoromethyl)-4,5,6,7,9,9a,10,11,12,12a-decahydrocyclopenta[c][1,4]diazepino[6,7,1-ij]quinoline;
1-fluoro-2-methoxy-4,5,6,7,9,9a,10,11,12,12a-decahydrocyclopenta[c][1,4]diazepino[6,7,1-ij]quinoline;
or pharmaceutically acceptable salts thereof.

8. The compound of claim 1 which is
4,5,6,7,9,9a,10,11,12,12a-decahydrocyclopenta[c][1,4]diazepino [6,7,1-ij] quinoline; or a pharmaceutically acceptable salt thereof.

9. The compound of claim 1 which is
(−)-4,5,6,7,9,9a,10,11,12,12a-decahydrocyclopenta[c][1,4]diazepino[6,7,1-ij]quinoline, or a pharmaceutically acceptable salt thereof.

10. The compound of claim 1 which is
4,5,6,7,9a,10,11,12,13,13a-decahydro-9H-[1,4]diazepino [6,7,1-de] phenanthridine or a pharmaceutically acceptable salt thereof.

11. The compound of claim 1 selected from
4,5,6,7,9,9a,10,11,12,13,14,14a-dodecahydrocyclohepta [c][1,4]diazepino [6,7,1-ij]quinoline;
2-bromo-4,5,6,7,9,9a,10,11,12,13,14,14a-dodecahydrocyclohepta[c][1,4]diazepino[6,7,1-ij]quinoline;
2-chloro-4,5,6,7,9,9a,10,11,12,13,14,14a-dodecahydrocyclohepta[c][1,4]diazepino[6,7,1-ij]quinoline;
1-fluoro-4,5,6,7,9,9a,10,11,12,13,14,14a-dodecahydrocyclohepta[c][1,4]diazepino[6,7,1-ij]quinoline;
1-fluoro-2-methoxy-4,5,6,7,9,9a,10,11,12,13,14,14a-dodecahydrocyclohepta[c][1,4]diazepino[6,7,1-ij] quinoline;
or pharmaceutically acceptable salts thereof.

12. The compound of claim 11 which is
4,5,6,7,9,9a,10,11,12,13,14,14a-dodecahydrocyclohepta [c][1,4]diazepino [6,7,1-ij]quinoline; or a pharmaceutically acceptable salt thereof.

13. The compound of claim 12 selected from:
(9aR,14aS)-4,5,6,7,9,9a,10,11,12,13,14,14a-dodecahydrocyclohepta[c][1,4]diazepino[6,7,1-ij]quinoline;
(9aS,14aR)-4,5,6,7,9,9a,10,11,12,13,14,14a-dodecahydrocyclohepta[c][1,4]diazepino[6,7,1-ij]quinoline;
or pharmaceutically acceptable salts thereof.

14. The compound of claim 1 selected from
5-acetyl-4,5,6,7,9,9a,10,11,12,12a-decahydrocyclopenta[c][1,4] diazepino[6,7,1-ij]quinoline;
benzyl 2-bromo-6,7,9,9a,10,11,12,12a-octahydrocyclopenta[c][1,4] diazepino[6,7,1-ij]quinoline-5(4H)-carboxylate;
benzyl 2-chloro-6,7,9,9a,10,11,12,12a-octahydrocyclopenta[c][1,4]diazepino[6,7,1-ij]quinoline-5(4H)-carboxylate;
benzyl 2-phenyl-6,7,9,9a,10,11,12,12a-octahydrocyclopenta[c][1,4] diazepino[6,7,1-ij]quinoline-5(4H)-carboxylate;
benzyl 2-methoxy-6,7,9,9a,10,11,12,12a-octahydrocyclopenta[c][1,4] diazepino[6,7,1 -ij]quinoline-5(4H)-carboxylate;
benzyl 1-fluoro-6,7,9,9a,10,11,12,12a-octahydrocyclopenta[c][1,4] diazepino[6,7,1-ij]quinoline-5(4H)-carboxylate;
benzyl 1-(trifluoromethyl)-6,7,9,9a,10,11,12,12a-octahydrocyclopenta[c][1,4] diazepino[6,7,1-ij]quinoline-5(4H)-carboxylate;
or pharmaceutically acceptable salts thereof.

15. The compound of claim 14 selected from
(−)-5-acetyl-4,5,6,7,9,9a,10,11,12,12a-decahydrocyclopenta[c][1,4] diazepino [6,7,1-ij]quinoline;
(+)-5-acetyl-4,5,6,7,9,9a,10,11,12,12a-decahydrocyclopenta[c][1,4] diazepino[6,7,1-ij]quinoline;
or pharmaceutically acceptable salts thereof.

16. The compound of claim 1 which is benzyl 6,7,9a,10,11,12,13,13a-octahydro-9H-[1,4]diazepino[6,7,1-de]phenanthridine-5(4H)-carboxylate; or a pharmaceutically acceptable salt thereof.

17. The compound of claim 1 selected from
5-acetyl-4,5,6,7,9,9a,10,11,12,13,14,14a-dodecahydrocyclohepta[c][1,4]diazepino[6,7,1-ij]quinoline;
benzyl 2-bromo-6,7,9,9a,10,11,12,13,14,14a-decahydrocyclohepta[c][1,4]diazepino[6,7,1-ij]quinoline-5(4H)-carboxylate;
benzyl 2-chloro-6,7,9,9a,10,11,12,13,14,14a-decahydrocyclohepta[c][1,4]diazepino[6,7,1-ij]quinoline-5(4H)-carboxylate;
benzyl 1-fluoro-6,7,9,9a,10,11,12,13,14,14a-decahydrocyclohepta[c][1,4]diazepino[6,7,1-ij]quinoline-5(4H)-carboxylate;
benzyl 1-fluoro-2-methoxy-6,7,9,9a,10,11,12,13,14,14a-decahydrocyclohepta[c][1,4]diazepino[6,7,1-ij]quinoline-5(4H)-carboxylate;
or pharmaceutically acceptable salts thereof.

18. The compound of claim 17 selected from
(9aR,14aS)-5-acetyl-4,5,6,7,9,9a,10,11,12,13,14,14a-dodecahydrocyclohepta[c][1,4]diazepino[6,7,1-ij]quinoline;
(9aS,14aR)-5-acetyl-4,5,6,7,9,9a,10,11,12,13,14,14a-dodecahydrocyclohepta[c][1,4]diazepino[6,7,1-ij]quinoline;
or pharmaceutically acceptable salts thereof.

19. A method of treating a mammal suffering from a condition selected from schizophrenia, schizophreniform disorder, schizoaffective disorder, delusional disorder, substance-induced psychotic disorder, L-DOPA-induced psychosis, psychosis associated with Alzheimer's dementia, psychosis associated with Parkinson's disease, psychosis associated with Lewy body disease, dementia, memory deficit, or intellectual deficit disorder associated with Alzheimer's disease comprising providing to the mammal suffering from the condition, a therapeutically effective amount of at least one compound of Formula I or a pharmaceutically acceptable salt thereof:

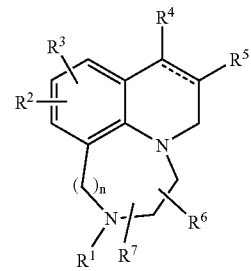

wherein
$R^1$ is hydrogen or alkyl of 1 to 6 carbon atoms;
$R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;
$R^4$ and $R^5$ are taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;
$R^6$ and $R^7$ are each, independently, hydrogen or alkyl of 1 to 6 carbon atoms;
n is 1 ; and
a dotted line represents an optional double bond.

20. The method of claim 19 wherein the condition is schizophrenia.

21. The method of claim 19 wherein the mammal is human.

22. A method of treating a mammal suffering from a condition selected from bipolar disorders, depressive disorders, mood episodes, anxiety disorders, adjustment disorders, or eating disorders comprising providing to the mammal suffering from the condition, a therapeutically effective amount of at least one compound of Formula I or a pharmaceutically acceptable salt thereof:

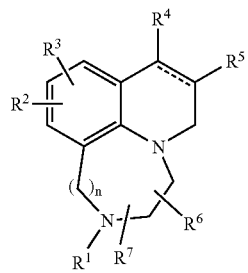

wherein
- $R^1$ is hydrogen or alkyl of 1 to 6 carbon atoms;
- $R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;
- $R^4$ and $R^5$ are taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;
- $R^6$ and $R^7$ are each, independently, hydrogen or alkyl of 1 to 6 carbon atoms;
- n is 1; and
- a dotted line represents an optional double bond.

23. The method of claim 22 wherein the bipolar disorder is bipolar I disorder, bipolar II disorder, or cyclothymic disorder; the depressive disorder is major depressive disorder, dysthymic disorder, or substance-induced mood disorder; the mood episode is major depressive episode, manic episode, mixed episode, or hypomanic episode; the anxiety disorder is panic attack, agoraphobia, panic disorder, specific phobia, social phobia, obsessive compulsive disorder, posttraumatic stress disorder, acute stress disorder, generalized anxiety disorder, separation anxiety disorder, or substance-induced anxiety disorder.

24. The method of claim 22 wherein the condition is depressive disorder, bipolar disorder or mood episode.

25. The method of claim 22 wherein the mammal is human.

26. A method of treating a mammal suffering from a condition selected from epilepsy, sleep disorders, migraines, sexual dysfunction, gastrointestinal disorders, or obesity comprising providing to the mammal suffering from the condition, a therapeutically effective amount of at least one compound of Formula I or a pharmaceutically acceptable salt thereof:

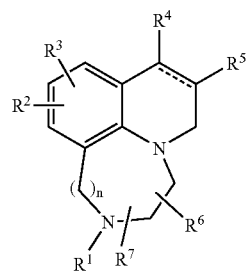

wherein
- $R^1$ is hydrogen or alkyl of 1 to 6 carbon atoms;
- $R^2$ and $R^3$ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any $R^2$ or $R^3$ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;
- $R^4$ and $R^5$ are taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by $R^4$ and $R^5$ may optionally be substituted with 1 to 3 substituents independently selected from a halogen atom, a $C_1$–$C_6$ alkyl group, or a $C_1$–$C_6$ alkoxy group;
- $R^6$ and $R^7$ are each, independently, hydrogen or alkyl of 1 to 6 carbon atoms;
- n is 1; and
- a dotted line represents an optional double bond.

27. The method of claim 26 wherein the condition is obesity.

28. The method of claim 26 wherein the mammal is a human.

29. A method of treating a mammal suffering from a central nervous system deficiency associated with trauma, stroke, or spinal cord injury comprising providing to the mammal suffering from the condition, a therapeutically effective amount of at least one compound of Formula I or a pharmaceutically acceptable salt thereof:

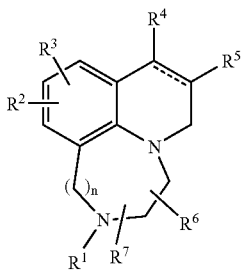

wherein
R¹ is hydrogen or alkyl of 1 to 6 carbon atoms;
R² and R³ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any R² or R³ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;
R⁴ and R⁵ are taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by R⁴ and R⁵ may optionally be substituted with 1 to 3 substituents independently selected from a halogen atom, a $C_1$–$C_6$ alkyl group, or a $C_1$–$C_6$ alkoxy group;
R⁶ and R⁷ are each, independently, hydrogen or alkyl of 1 to 6 carbon atoms;
n is 1 ; and
a dotted line represents an optional double bond.

30. A pharmaceutical composition comprising
a) at least one compound of Formula I or a pharmaceutically acceptable salt thereof:

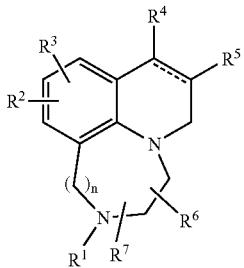

wherein
R₁ is hydrogen or alkyl of 1 to 6 carbon atoms;
R² and R³ are each, independently, hydrogen, hydroxy, alkyl of 1–6 carbon atoms, alkoxy of 1–6 carbon atoms, halogen, carboxamido, carboalkoxy of two to six carbon atoms, perfluoroalkyl of 1–6 carbon atoms, cyano, alkanesulfonamido of 1–6 carbon atoms, alkanesulfonyl of 1–6 carbon atoms, alkanamido of 1–6 carbon atoms, amino, alkylamino of 1–6 carbon atoms, dialkylamino of 1–6 carbon atoms per alkyl moiety, perfluoroalkoxy of 1–6 carbon atoms, alkanoyloxy of 2 to 6 carbon atoms, alkanoyl of 2 to 6 carbon atoms, aroyl of 6 to 8 carbon atoms, aryl of 5 to 7 carbon atoms, a $C_6$ to $C_{13}$ alkylaryl group having 5 to 7 carbon atoms in the aryl moiety, a 5 to 7 membered heteroaryl group, or a 6 to 13 membered alkylheteroaryl group having 5 to 7 members in the heteroaryl moiety, wherein any R² or R³ substituent having an aryl or heteroaryl moiety may optionally be substituted on the aryl or heteroaryl moiety with 1 to 3 substituents independently selected from a halogen atom, a $C_1$–$C_6$ alkyl group, or a $C_1$–$C_6$ alkoxy group;
R⁴ and R⁵ are taken together with the carbons to which they are attached, form a cyclic moiety selected from a cycloalkane of 4 to 8 carbon atoms, cycloalkene of 4 to 8 carbon atoms, bridged bicyclic alkane of 5 to 10 carbon atoms, bridged bicyclic alkene of 5 to 10 carbon atoms, pyran or thiopyran in which the sulfur atom is optionally oxidized to the sulfoxide or sulfone, wherein the cyclic moiety formed by R⁴ and R⁵ may optionally be substituted with 1 to 3 substituents independently selected from a halogen atom, a $C_1$–$C_6$ alkyl group, or a $C_1$–$C_6$ alkoxy group;
R⁶ and R⁷ are each, independently, hydrogen or alkyl of 1 to 6 carbon atoms;
n is 1 ; and
a dotted line represents an optional double bond; and
b) at least one pharmaceutically acceptable carrier or excipient.

31. The composition of claim 30 wherein R² and R³ are independently selected from hydrogen, halo, trifluoromethyl, phenyl or alkoxy of 1 to 3 carbon atoms; R¹, R⁶ and R⁷ are each hydrogen; and R⁴ and R⁵, taken together with the carbon atoms to which they are attached, form cyclopentane, cyclohexane or cycloheptane.

32. The composition of claim 30 wherein the compound is at least selected from 4,5,6,7,9,9a,10,11,12,12a-decahydrocyclopenta[c][1,4]diazepino[6,7,1-ij]quinoline or a pharmaceutically acceptable salt thereof.

33. A pharmaceutical composition comprising:
a) a compound of formula (V) or a pharmaceutically acceptable salt thereof

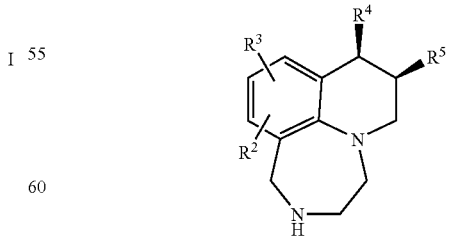

wherein
R² and R³ are each hydrogen; and
R⁴ and R⁵, taken together with the carbon atoms to which they are attached, form cyclopentane; and b) at least one pharmaceutically acceptable carrier or excipient.

34. A method of treating a mammal suffering from a condition selected from at least one of schizophrenia, schizophreniform disorder, or schizoaffective disorder comprising providing to a mammal, a therapeutically effective amount of at least one compound of formula (VIII) or a pharmaceutically acceptable salt thereof

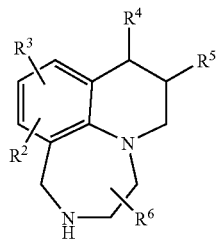

VIII wherein
R², R³ and R⁶ are each hydrogen; and
R⁴ and R⁵' taken together with the carbon atoms to which they are attached, form cyclopentane.

35. The method of claim 34 wherein the mammal is human and the compound administered comprises a compound of formula V or a pharmaceutically acceptable salt thereof

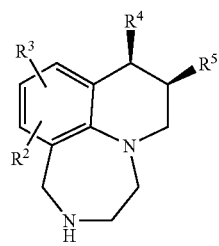

V wherein
R² and R³ are each hydrogen; and
R⁴ and R⁵' taken together with the carbon atoms to which they are attached, form cyclopentane.

36. The method of claim 35 wherein the condition is schizophrenia.

37. A method of treating a mammal suffering from obesity comprising providing to a mammal, a therapeutically effective amount of at least one compound of formula (VIII) or a pharmaceutically acceptable salt thereof

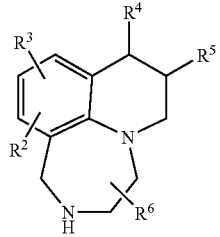

VIII wherein
R²' R³ and R⁶ are each hydrogen; and
R⁴ and R⁵' taken together with the carbon atoms to which they are attached, form cyclopentane.

38. The method of claim 37 wherein the mammal is human and the compound administered comprises a compound of formula V or a pharmaceutically acceptable salt thereof

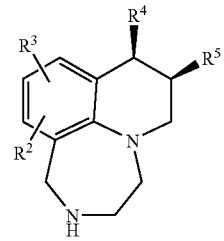

V wherein
R² and R³ are each hydrogen; and
R⁴ and R⁵' taken together with the carbon atoms to which they are attached, form cyclopentane.

39. A method of treating a mammal suffering from a condition selected from at least one of depressive disorders, bipolar disorders, or mood episodes comprising providing to a mammal, a therapeutically effective amount of at least one compound of formula (VIII) or a pharmaceutically acceptable salt thereof

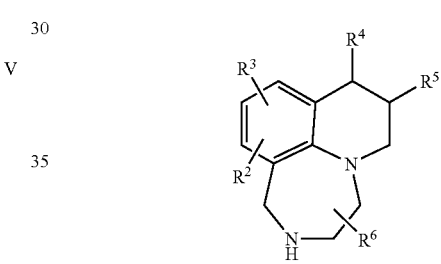

VIII wherein
R² and R³ and R⁶ are each hydrogen; and
R⁴ and R⁵' taken together with the carbon atoms to which they are attached, form cyclopentane.

40. The method of claim 39 wherein the mammal is human and the compound administered comprises a compound of formula V or a pharmaceutically acceptable salt thereof

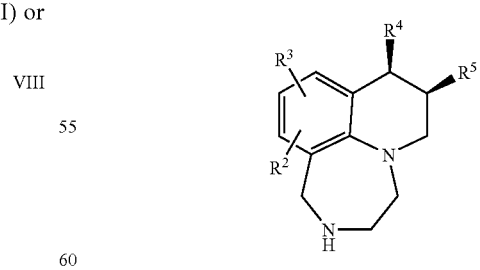

V wherein
R² and R³ are each hydrogen; and
R⁴ and R⁵, taken together with the carbon atoms to which they are attached, form cyclopentane.

41. The method of claim 40 wherein the condition is depressive disorders.

42. The method of claim 41 wherein the condition is major depressive disorder.

43. The method of claim 40 wherein the condition is bipolar disorders.

44. The method of claim 40 wherein the condition is mood episodes.

45. The method of claim 44 wherein the condition is major depressive episode.

46. A compound of formula (VIII) or a pharmaceutically acceptable salt thereof

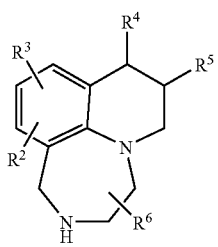

VIII wherein
$R^2$, $R^3$ and $R^6$ are each hydrogen; and
$R^4$ and $R^5$, taken together with the carbon atoms to which they are attached, form cyclopentane.

47. A compound of formula V or a pharmaceutically acceptable salt thereof

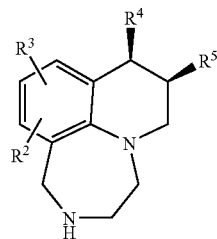

V wherein
$R^2$ and $R^3$ are each hydrogen; and
$R^4$ and $R^5$ taken together with the carbon atoms to which they are attached, form cyclopentane.

48. The compound of claim 47 that is (−)-4,5,6,7,9,9a,10,11,12,12a-decahydrocyclopenta [c][1,4]diazepino[6,7,-ij] quinoline hydrochloride.

49. A compound of formula IV or a pharmaceutically acceptable salt thereof

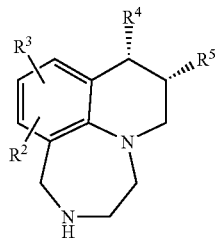

IV wherein
$R^2$ and $R^3$ are each hydrogen; and
$R^4$ and $R^5$, taken together with the carbon atoms to which they are attached, form cyclopentane.

50. The compound of claim 49 wherein the pharmaceutically acceptable salt is hydrochloride.

51. The composition of claim 30 wherein the compound comprises a compound of formula IV or a phannaceutically acceptable salt thereof

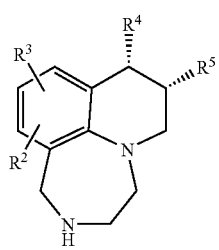

IV wherein
$R^2$ and $R^3$ are each hydrogen; and
$R^4$ and $R^5$, taken together with the carbon atoms to which they are attached, form cyclopentane.

52. The compound of claim 46 that is 4,5,6,7,9,9a,10,11,12,12a-decahydrocyclopenta [c][1,4]diazepino[6,7,1-ij] quinoline hydrochloride.

* * * * *